United States Patent
Koch et al.

(10) Patent No.: US 7,470,792 B2
(45) Date of Patent: Dec. 30, 2008

(54) PROCESS FOR THE PREPARATION OF EPOTHILONE DERIVATIVES, NEW EPOTHILONE DERIVATIVES AS WELL AS NEW INTERMEDIATE PRODUCTS FOR THE PROCESS AND THE METHODS OF PREPARING SAME

(75) Inventors: Guido Koch, Riehen (CH); Olivier Loiseleur, Saint-Louis (FR)

(73) Assignee: Novartis AG, Basel (CH)

( * ) Notice: Subject to any disclaimer, the term of this patent is extended or adjusted under 35 U.S.C. 154(b) by 131 days.

(21) Appl. No.: 10/526,283

(22) PCT Filed: Sep. 12, 2003

(86) PCT No.: PCT/EP03/10171

§ 371 (c)(1),
(2), (4) Date: Sep. 1, 2005

(87) PCT Pub. No.: WO2004/024735

PCT Pub. Date: Mar. 25, 2004

(65) Prior Publication Data

US 2006/0106073 A1     May 18, 2006

(30) Foreign Application Priority Data

Sep. 13, 2002 (GB) ................. 0221312.2

(51) Int. Cl.
*C07D 417/14* (2006.01)
*C07D 313/00* (2006.01)
(52) U.S. Cl. ..................................... 548/181; 549/270
(58) Field of Classification Search ............... 548/181; 549/270
See application file for complete search history.

(56) References Cited

FOREIGN PATENT DOCUMENTS

| WO | WO 98/25929 | 6/1998 |
| WO | WO 99/54330 | 10/1999 |
| WO | WO 01/07439 | 2/2001 |
| WO | WO 02/30356 | 4/2002 |
| WO | WO 2004/012735 | 2/2004 |

OTHER PUBLICATIONS

Nicolaou et al., "Total Synthesis of 16-Desmethylepothilone B, Epothilone B10, Epothilone F, and Related Side Chain Modified Epothilone B Analogues", *Chem Euro J*, vol. 6, No. 15, pp. 2783-2800 (2000).

Höfle, Glaser, Leibold and Sefkow, "Epothilone A-D and Their Thiazole-Modified Analogs as Novel Anticancer Agents", *Pure Appl Chem*, vol. 71, No. 11, pp. 2019-2024 (1999).

*Primary Examiner*—Rei-tsang Shiao
*Assistant Examiner*—Joseph R Kosack
(74) *Attorney, Agent, or Firm*—George R. Dohmann

(57) ABSTRACT

The present invention provides a synthesis for the preparation of epothilone derivatives of formula 9

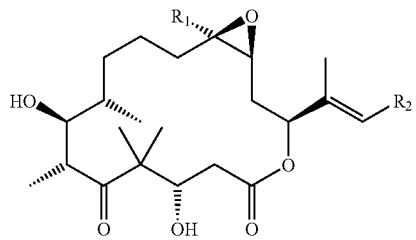

wherein R1 is methyl, and R2 is an unsubstituted or substituted aryl; an unsubstituted or substituted heteroaryl; or an unsubstituted or substituted heterocyclic radical fused to a benzene nucleus; and salts thereof, and intermediates for the synthesis of a compound of formula 9.

13 Claims, No Drawings

PROCESS FOR THE PREPARATION OF EPOTHILONE DERIVATIVES, NEW EPOTHILONE DERIVATIVES AS WELL AS NEW INTERMEDIATE PRODUCTS FOR THE PROCESS AND THE METHODS OF PREPARING SAME

The invention relates to a new process for the production of epothilone derivatives having not only the 2-methyl-thiazole substituent but, for example, other heteroaryl or aryl substituents or heterocyclic radicals fused to a benzene nucleus and methyl as substituent in 12-position within the epothilone structure, new epothilone derivatives as well as intermediate products for the process and methods for preparing them. Said intermediates are new compounds as such and part of the invention.

The epothilones (16-membered macrolides which were initially isolated from the myco-bacterium *Sorangium cellulosum*) represent a class of promising anti-tumor agents, and have been found to be potent against various cancer lines, including breast cancer cell lines.

These agents have the same biological mechanism of action as Taxol, an anti-cancer drug currently used as primary therapy for the treatment of breast cancer and have been reported to be more potent than Taxol.

Potential applications of the epothilones are the treatment of Alzheimer's disease, malaria and diseases caused by gram-negative organisms. In particular, epothilones are suitable for the treatment of proliferative diseases.

The term "proliferative disease" relates especially to solid tumor diseases, liquid tumors, e.g. leukemia, and psoriasis.

The term "solid tumor disease" especially means breast cancer, cancer of the colon and generally the GI tract including gastric cancer, hepatoma; lung cancer, in particular small-cell lung cancer and non-small-cell lung cancer, renal cancer, mesothelioma, glioma, squamous cell carcinoma of the skin, head and neck cancer, genitourinary cancer, e.g. cervical, uterine, ovarian, testicles, prostate or bladder cancer; Hodgkin's disease, carcinoid syndrome or Kaposl's sarcoma.

Epothilone derivatives are already described, e.g., in WO 97/19086. These derivatives are produced starting from natural epothilone A and B.

The total synthesis of epothilone A is described by Schinzer et al in Chem. Eur. J. 1996, 2, No. 11, 1477-1482. Another synthesis of epothilone A and B and derivatives is described by K. C. Nicolaou et al. in Angew. Chem. 1997, 109, 170-172 and Nature, Vol. 387, 1997, 268-272.

In Chem. Commun. 1997, pp. 2343-2344, K. C. Nicolaou et al describe a total synthesis of 26-hydroxy-epothilone B and related compounds involving a selective Wittig olefination reaction, an aldol reaction and macrolactonization as key steps. In more detail the total synthesis of 26-hydroxy-epothilone B and related analogues via a macrolactonization based strategy has been described in Tetrahedron 54 (1998), 7127-7166 by K. C. Nicolaou et al.

Furthermore in WO 98/25029 K. C. Nicolaou et al describe and claim the synthesis of epothilone A, epothilone B, epothilone analogues, libraries of epothilone analogues by using solid phase and solution phase chemistries.

The embodiment and goal of the present invention is to overcome all the drawbacks of the known processes and to provide a more simple and improved process for the preparation of the above mentioned epothilones and epothilone derivatives and salts thereof which is also feasible on industrial scale by shortening the sequence of the synthetic route and which process constitutes a basis of high overall yield in average and provides precursors and final products of high purity.

A synthesis for the preparation of epothilone derivatives of formula 9

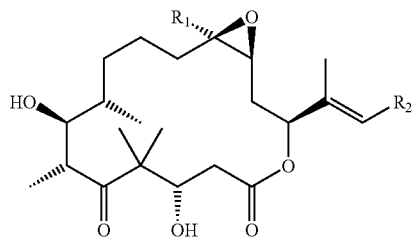

wherein

R1 is methyl, and

R2 has the meaning of an unsubstituted or substituted aryl, an unsubstituted or substituted heteroaryl or an unsubstituted or substituted heterocyclic radical fused to a benzene nucleus, and salts thereof.

The prefix "lower" denotes a radical having up to and including a maximum of 6, especially up to and including a maximum of 4 carbon atoms, the radicals in question being either unbranched or branched with single or multiple branching.

R2 as unsubstituted or substituted aryl is preferably an aromatic radical with 6 to 14 carbon atoms, especially phenyl, naphthyl, fluorenyl or phenanthrenyl, whereby the said radical is unsubstituted or is substituted by one or more substituents, preferably up to three, primarily one or two substituents, especially those selected from amino; lower alkanoylamino, especially acetylamino; halogen, especially fluorine, chlorine or bromine; lower alkyl, especially methyl or also ethyl or propyl; halogen-lower alkyl, especially trifluoromethyl; hydroxy; lower alkoxy, especially methoxy or also ethoxy; phenyl-lower alkoxy, especially benzyloxy; nitro, cyano, $C_8$-$C_{12}$-alkoxy, especially n-decyloxy, carbamoyl, lower alkyl-carbamoyl, such as N-methyl- or N-tert-butylcarbamoyl, lower alkanoyl, such as acetyl, phenyloxy, halogen-lower alkyloxy, such as trifluoromethoxy or 1,1,2,2-tetrafluoroethyloxy, lower alkoxycarbonyl, such as ethoxycarbonyl, lower alkylmercapto, such as methyl-mercapto, halogen-lower alkylmercapto, such as trifluoromethylmercapto, hydroxy-lower alkyl, such as hydroxymethyl or 1-hydroxymethyl, lower alkanesulphonyl, such as methanesulphonyl, halogen-lower alkanesulphonyl, such as trifluoromethanesulphonyl, phenylsulphonyl, dihydroxybora (—B(OH)$_2$), 2-methyl-pyrimidin-4-yl, oxazol-5-yl, 2-methyl-1,3-dioxolan-2-yl, 1H-pyrazol-3-yl, 1-methyl-pyrazol-3-yl; and lower alkylenedioxy which is bonded to two adjacent carbon atoms, such as methylenedioxy.

R2 as aryl is especially phenyl.

Halogen is especially fluorine, chlorine, bromine, or iodine, in particular fluorine or chlorine.

R2 being an unsubstituted or substituted heteroaryl is, for example, a radical selected from following structures:

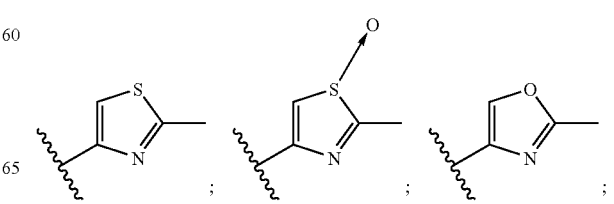

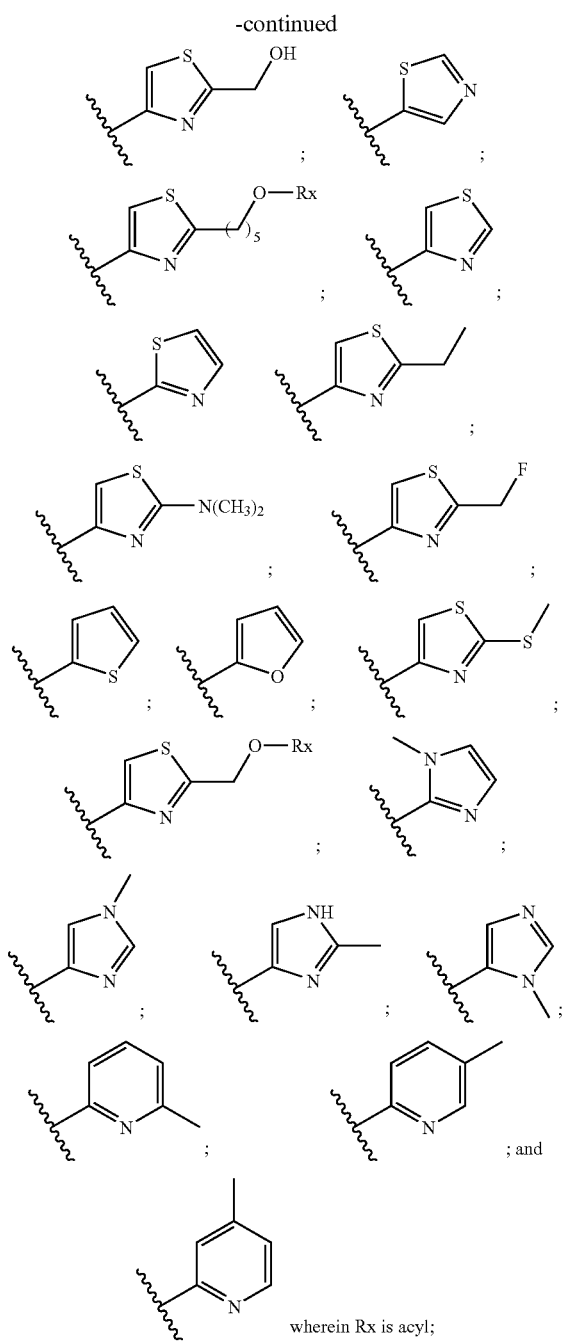

wherein Rx is acyl;

R2 as heterocyclic radical being fused to a benzene nucleus is a radical selected for example from the radicals of formulae

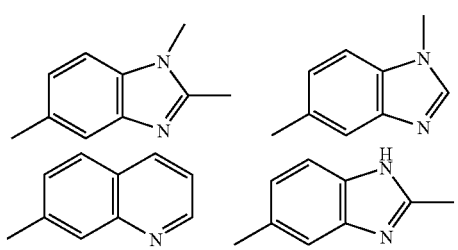

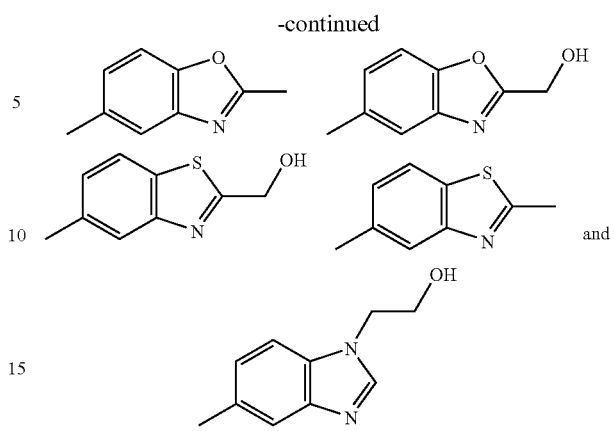

and

The new synthesis comprises following sequences:
a) reacting a compound of formula 1

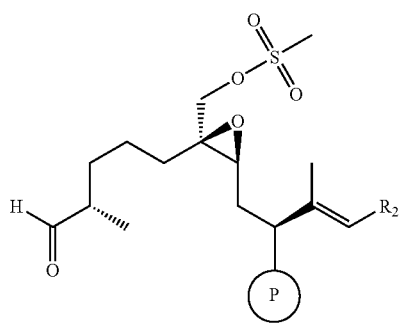

(1)

wherein R2 has the meanings given above and the mesylate group may be replaced by a tosylate group and the like and

Ⓟ is an alcohol protecting group preferably a silyl protecting group, more preferably any of the later on listed silylether forming groups and most preferably a lower alkyl silyl protecting group preferably selected from TES, TBDS, TPS, with a sultam derived compound of formula 2 as, for example,

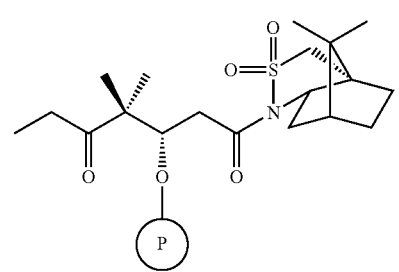

(2)

wherein

is an alcohol protecting group preferably a silyl protecting group, more preferably any of the later on listed silylether forming groups and most preferably a lower alkyl silyl protecting group preferably selected from TES, TBDS, TPS, in a selective aldol reaction in the presence of a Lewis acid and addition of a base in an inert solvent at lower temperatures between −50 to −100° C. and thereafter at elevated temperatures between −20 to +20° C. obtaining a compound of formula 3

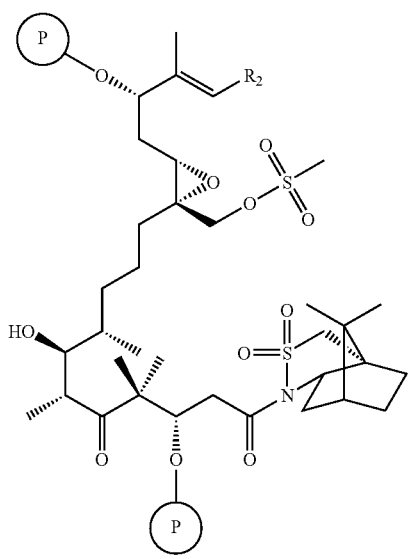

(3)

wherein R2 has the meanings given above.

The compound of formula 2 as given above may be replaced by a compound of formula 2 wherein

is an alcohol protecting group preferably a silyl protecting group, more preferably any of the later on listed silylether forming groups and most preferably a lower alkyl silyl protecting group preferably selected from TES, TBDS, TPS.

The compounds of formula 3 are new compounds and are used as intermediates for the next step b) of the process sequence, and b) the obtained compounds of above formula 3 are reacted at temperatures between −70 and +25° C. in the presence of a silyl-ether forming compound and in the presence of 2,6-lutidine forming compounds of formula 4

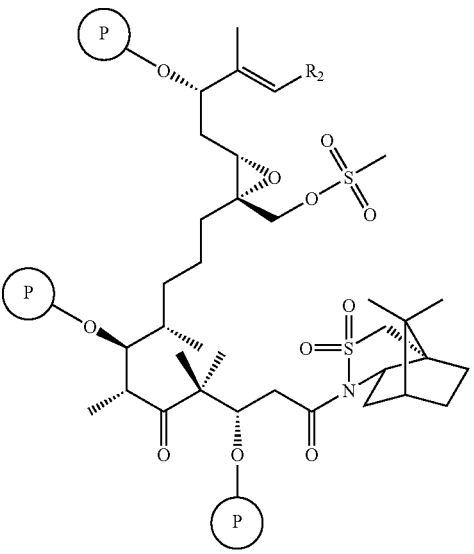

(4)

wherein R2 and

have the meanings given above.

The compounds of formula 4 are new compounds and are used as precursors for the next step c) of the process sequence, and c) converting an above compound of formula 4 to the carboxylic acid by splitting off the chiral auxiliary group with TBAOH/H2O2 in DME or LiO2H In THF/MeOH/H2O obtaining compound of formula 5

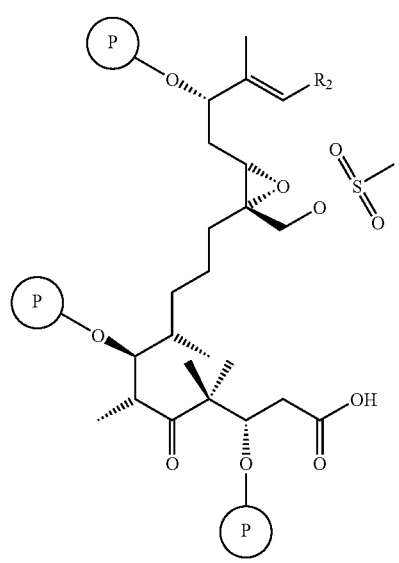

(5)

wherein R2 and

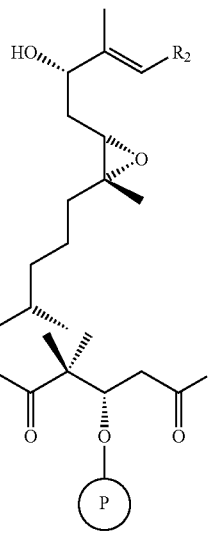

have the meanings given above.

The obtained compounds of formula 5 are new compounds and used as further intermediates for the next step d) of the process sequence, and d) reacting a compound of above formula 5 with a reducing reagent in an inert solvent cleaving the mesylate group or tosylate group or the like obtaining a compound of formula 6

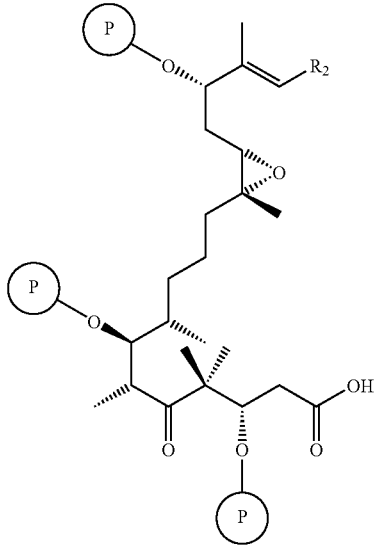

wherein R2 and (P)

have the above given meanings.

The obtained compounds of formula 6 are new compounds and are used as intermediates for the next step e) of the process sequence, and e) hydrolysing the tri-protected tris-silylether compounds of above formula 6 with a desilylation reagent or an acid in an inert solvent or a mixture thereof, e.g. TASF or HF-pyridine in THF, obtaining a selectively desilytated compound of formula 7

(7)

wherein R2 and (P)

have the above given meanings.

The compounds of formula 7 are new compounds and are used as precursors for the next step f) of the process sequence, and f) macrolactonizing obtained compounds of formula 7 according to the conditions described by M. Yamaguchi et al Bull. Chem. Soc. Jpn., 1979, 52, 1989, obtaining a fully protected epothilone derivative of formula 8

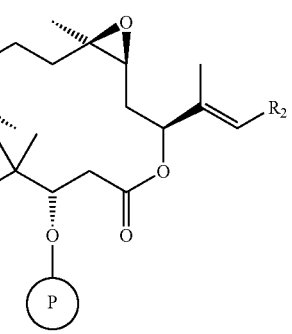

wherein R2 and (P)

have the above defined meanings.

The obtained compounds of formula 8 are new compounds and are used as precursors for the next step g) of the process sequence, and g) treating an obtained compound of formula 8 with HF-pyridine in an inert solvent at temperatures between 0°-30° C. and cleaving both silyl ether protecting groups obtaining epothilone derivatives of formula 9

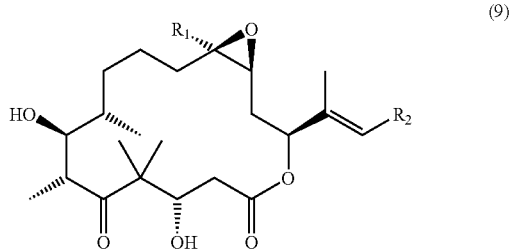

(9)

wherein R1 is methyl and R2 has the above described meanings and optionally converting compounds of formula 9 to a salt with metal cations by conventional methods.

The transformation of epothilone B to the corresponding lactam is disclosed in Scheme 21 (pages 31 and 32) and Example 3 of WO99/02514 (pages 48-50). The transformation of a compound of formula 9 which is different from epothilone B into the corresponding lactam compound may be achieved analogously.

Inert solvents mentioned in one of the reaction steps a) to g) encompass, but are not limited to methanol, ethanol, propanol, dichloromethane, dichloroethane, DMF, tetrahydrofuran (THF), benzene, toluene, pyridine, ethylacetate, acetone or t-butyl-methyl ether (TBME), hexane or heptane and the like and mixtures thereof.

Organic bases mentioned in one of the reaction steps a) to g) encompass, but are not limited to organic amines such as unsubstituted or hydroxy-substituted mono-, di- or tri-alkylamines, especially mono-, di- or tri-lower alkyl-amines, e.g. methylamine, dimethylamine, di-n-propylamine, triethylamine, tri-n-propylamine, tri-n-butylamine and di-isopropylethylamine ($iPr_2Net$), as nitrogen heterocycles, ethyleneimine, pyrrolidine, piperidine and morpholine, especially 4-dimethylamino-pyridine (DMAP), pyridine, 2,6-lutidine, 2,6-di-tert-butylpyridine and the like.

Metalo-organic bases are e.g. LDA (lithium diisopropylamine), BuLi, sec.BuLi, KHMDS, LiHMDS, or NaHMDS.

Reducing agents are e.g. DIBAL-H (diisobutylaluminium-hydride), LiAlH4 (Lithiumaluminium-hydride), lithium triethylboro-hydride and the like.

(P)

are alcohol protecting groups commonly used in organic synthesis and should protect the functional hydroxy groups against unwanted secondary reactions. Silyl-ether forming compounds are for example standard protecting groups used very commonly in organic synthesis and preferably a silyl protecting group is lower alkylsilyl more preferably a silyl protecting group is selected from TMS (trimethyl-silyl), TES (triethyl-silyl), TPS(tri-n-propylsilyl), TBDS(tertiary-butyl-dimethylsilyl), DEIPS(diethyl-isopropyl-silyl), IPDMS (dimethyl-isopropy-lsilyl), TDS(thexyl-dimethylsilyl), TIPS (tri-isopropyl-silyl), THP (tetrahydropyranyl-silyl) or the like, preferably TES, TPS or TBDMS most preferably TPS. If a compound contains more than one protecting group the protecting groups are selected independently of each other and may be all the same, all different or any combination thereof, preferably the protecting groups are all the same, most preferably the protecting groups will be TPS.

The term pharmaceutically acceptable metal salts contemplates salts formed with the sodium, potassium, calcium, magnesium, aluminium, iron and zinc ions. The salts are prepared by conventional methods.

Suitable acids for cleaving the bis-trimethylsilanyloxy groups of the compound of formula 4 by hydrolysis are weak organic acids which do not open the epoxide ring of the epothilone structure and are for example dilute acetic acid, propionic acid, glycolic acid, lactic acid, fumaric acid, succinic acid, adipic acid, pimelic acid, suberic acid, azelaic acid, malic acid, tartaric acid, maleic acid, mandelic acid, amino acids, such as glutamic acid or aspartic acid, especially citric acid and the like. Especially may be mentioned HF.pyridine in THF or HF.pyridine in pyridine.

Chiral auxiliary groups used for the aldol reaction according to a) of the process sequence are for example the sultam auxiliary group or oxazolidinone groups. e.g.

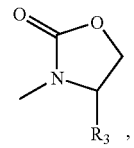

especially

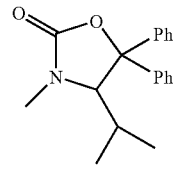

and other known chiral auxiliary groups.

The reaction steps a) to g) of the mentioned process sequence for the preparation of the compounds of formula 9 are carried out in more detail described as follows:

a) Compounds of formula 1 are reacted with a compound of formula 2 for example in the presence of TiCl4 and Hünig base (iPr2NET) in dichloromethane at a temperature of −78° C. and thereafter at a temperature of 0° C. obtaining new compounds of formula 3.

b) The obtained compounds of formula 3 are reacted with a silyl-ether forming compound e.g. TPSCl, TBDMSOTf in the presence of 2,6-lutidine at temperatures between −20° and 25° C., especially at a temperature of −10° C. in dichloromethane as inert solvent forming compounds of formula 4.

c) The obtained compounds of formula 4 are converted to the carboxylic acid by splitting off the sultam auxiliary group with TBAOH/H2O2 in DME or LiO2H in THF/MeOH/H2O obtaining a compound of formula 5.

d) The obtained compounds of formula 5 are reacted with LiBHET3 as reducing reagent in THF as inert solvent for cleaving the mesylate or tosylate group or the like obtaining a compound of formula 6.

e) The obtained compounds of formula 6 are hydrolysed with a desilylation reagent, especially with TASF or an organic acid, especially HF.pyridine in an inert solvent, e.g. pyridine or THF, obtaining compounds of formula 7.

f) The obtained compounds of formula 7 are macrolactonized according to Yamaguchi et al, e.g. treating the hydroxy acid with Et3N and 2,4,6-trichlorobenzoyl chloride at lower temperature, e.g. 0° C. and thereafter the reaction mixture is added to a solution of 4-DMAP In toluene and the temperature raised to ca. 75° C. obtaining compounds of formula 8.

g) The obtained protected epothilone derivatives of formula 8 are treated with HF-pyridine in pyridine as inert solvent and after cleavage of both silyl ether protecting groups (TPS, TES, TBDMS) epothilone derivatives of formula 9 are obtained, wherein R1 is methyl and R2 has the above described meanings and optionally converting compounds of formula 9 wherein R1 and R2 have the defined meanings under formula 9 to a salt with metal cations by conventional methods.

The used starting compounds for the process sequence of formula 1 wherein R2 has the meaning of an unsubstituted or substituted aryl, an unsubstituted or substituted heteroaryl or an unsubstituted or substituted heterocyclic radical fused to a benzene nucleus are used as key-intermediates for the preparation of epothilone derivatives of formula 9 are new and are prepared by following process sequence comprising steps a)-g), as given thereafter.

The detailed meanings of R2 and

have been defined under formula 9 and formula 1 respectively.

The new developed synthesis comprises following sequences:

a) reacting a compound of formula X

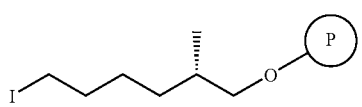

with PPH3 at temperatures between 50°-150° C., more precisely at a temperature 100° C. and thereafter with KHMDS in an inert solvent, especially in THF at 0° C. and thereafter cooling the reaction mixture to a temperature between −50° to −100° C., and treating with CH3CO2Cl more precisely at a temperature of −78° C. obtaining a compound of formula XI

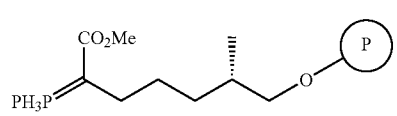

and, b) reacting the obtained compound of formula XI with a compound of formula XII

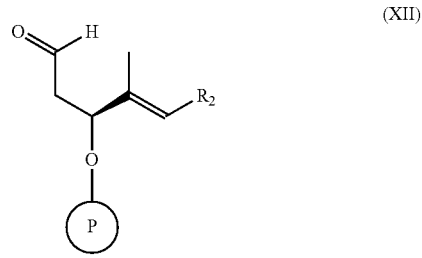

in an inert solvent, e.g. in toluene at temperatures between 20° to 60° C., more precisely at a temperature of 40° C. obtaining a compound of formula XIII

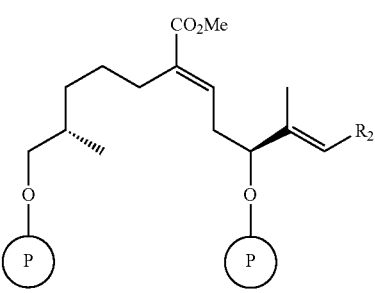

c) reducing a compound of formula (XIII) with a reducing agent, especially with DIBALH, in an inert solvent, e.g. toluene at temperatures between −50° to −100° C., more precisely at a temperature of −78° C. and thereafter elevating the temperature to 0° C. obtaining a compound of formula XIV

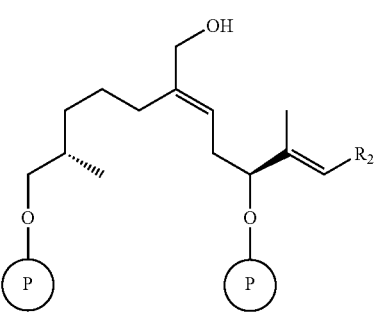

(the drawing of formula XIV and the following compounds thereafter have been simplified), R2 and

have the above meanings, and d) using the conditions under Sharpless [(+)-diethyl-L-tartrate, Ti(OPr)4, t-BuOOH] for epoxidation of a compound of formula XIV obtaining a compound of formula XV

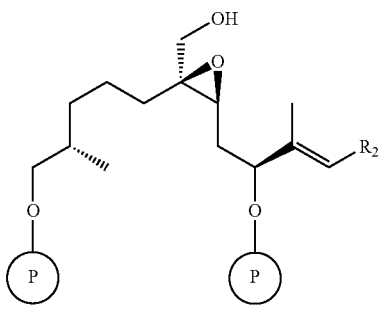 (XV)

wherein R2 and

have the above given meanings under formula 9 and formula 1 respectively.

The obtained compound of formula XV is a new compound and is used as precursor for the next step e) of the process sequence, and e) introducing the mesylate group into a compound of formula XV by adding mesylate chloride (the mesylate group may be replaced by a corresponding tosylate group or the like) in the presence of triethylamine (Et₃N) in an inert solvent, e.g. dichloromethane obtaining a compound of formula XVI

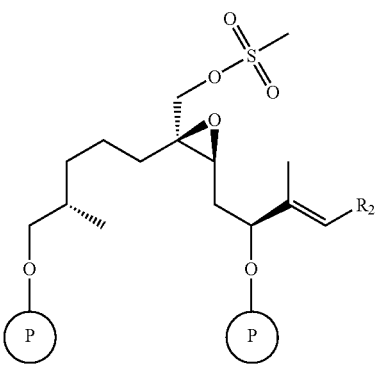 (XVI)

wherein R2 and

have the above given meaning.

The obtained compound of formula XVI is a new compound and is used as intermediate for the next step f), and f) treating the obtained compound of formula XVI with an organic acid in an inert solvent, more precisely with pyridinium p-toluenesulfonate or camphor sulfonic acid in absolute ethanol, hydrolysing the one protecting groups and obtaining a compound of formula XVII (XVII)

wherein R2 has the above given meanings, and g) oxidizing by using the Swern-oxidation method, e.g. oxidizing the alcoholic group by the promotion of oxalyl chloride and activation of dimethyl sulfoxide, passing the alkoxysulfonium salts and after addition of a base and intramolecularly rearrangement obtaining a keto compound of formula 1 used in the previous inventive process sequence as starting compound.

The inventive process sequence for producing epothilone derivatives of formula 9 shows many advantages in comparison with other known and published synthesis:

The early introduction of the epoxide avoids surprisingly a problematic epoxidation step at late intermediates within the synthesis sequence, A remarkable stabilization effect was detected for the mesylate and tosylate epoxides. Many steps can be carried out in the presence of these functional groups.

High yielding and highly diastereoselective titanium enolate aldol reaction between the α-branched aldehyde and the ethylketone key fragments could be achieved.

The aldol reaction tolerates surprisingly the presence of the mesylate and tosylate epoxide.

The aldol reaction allows a highly convergent synthesis of epothilone derivatives.

The aldol reaction allows surprisingly to make use of the chiral sultam auxiliary as carboxylate protecting group and therefore avoids additional time consuming reduction and oxidation steps prior to the final macrolactonisation step.

The inventive process sequence is a shorter synthetic route than any other published synthetic routes known in literature, furthermore a higher overall yield could be detected. All in all the summarized advantages underline the inventive step of mentioned process sequence.

A second aspect of the present invention are the novel intermediates, which are prepared according to the reaction described and are useful for the preparation of compounds of formula 9.

The epothilone derivatives of formula 9 for medical treatment may be administered by every known route and may be selected from the group consisting of the intravenous route, the intraarterial route, the intracutaneus route, the subcutaneous route, the oral route, the buccal route, the intramuscular route, the anal route, the transdermal route, the intradermal route, the intratechal route and the like.

Also sustained release formulations may be performed involving biodegradable microspheres, such as microspheres comprising polyacrylic acid, polyglycolic acid or mixtures of these.

The compounds of formula 9 of the invention can be used alone or in combination with other pharmaceutically active substances, e.g. with other chemotherapeuticals such as classical cytostatics. In the case of combinations with an other chemotherapeutic, a fixed combination of two or more components (e.g. kit of parts) are prepared as already known to a person of skill in the art, and the compound of the present invention and any other chemo-therapeutic are administered at an interval that allows common, additional or preferably synergistic effect for tumor treatment.

The following non limiting examples illustrate the inventor's preferred method for preparing the claimed compounds of the invention, which should not be construed as limiting the scope of this invention.

EXAMPLE 1

Compound X

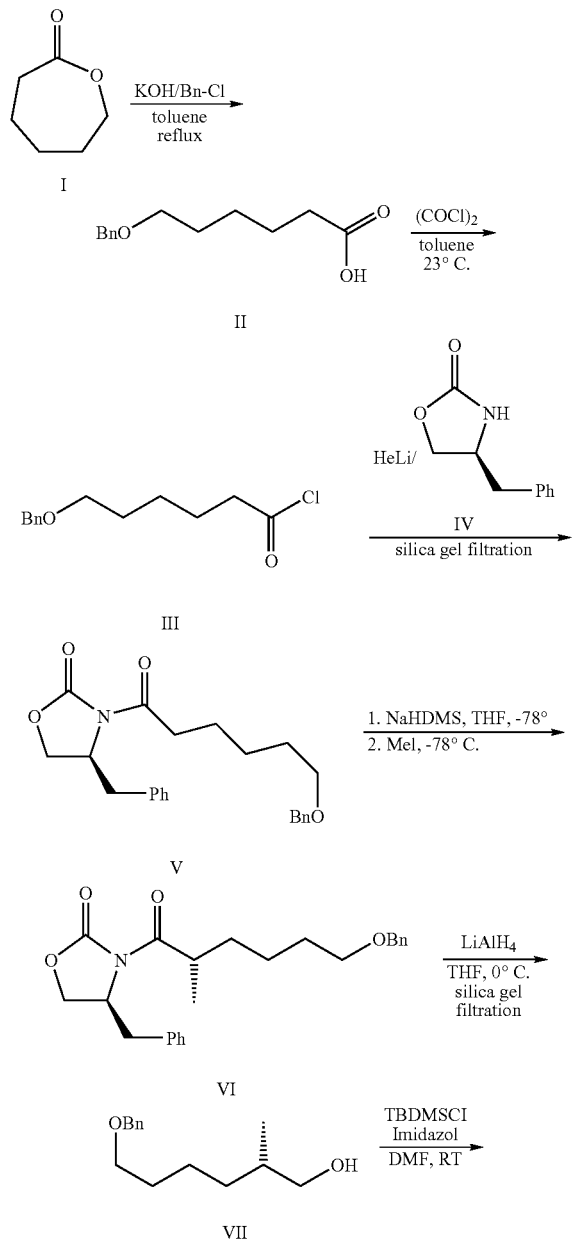

6-Benzyloxy-hexanoic acid (II) (*Can. J. Chem.* 1992, 70, 1427)

To a solution of 102.2 g (0.90 mol) of 6-caprolactone in 1.5 l of toluene was added 250.6 g (4.48 mol) of KOH and 113.3 ml (0.98 mol) of benzylchloride. The reaction mixture was stirred at reflux temperature for 20 h. The reaction was quenched with 1.7 l of water at room temperature. The aqueous layer was separated and the toluene layer was extracted with 200 ml of water. The combined aqueous phases were treated with 300 ml of HCl (conc.) at 12° C. to acidify the solution to pH 1.0. After extraction with 1.1 l of isopropyl acetate in two portions the combined organic extracts were washed with 300 ml of brine and dried over $MgSO_4$. Concentration under reduced pressure afforded 151.2 g (76%) of a the acid II as a yellowish oil. $R_f$=0.35 ($SiO_2$, 95:5 $CH_2Cl_2$—$CH_3OH$).

6-Benzyloxy-hexanoyl chloride (III)

The crude acid II (110 g, 0.50 mol) was dissolved in 320 ml of toluene. To the solution was added 140 µl of DMF followed by the addition of 56.7 ml (0.66 mol) of oxalylchloride. The reaction mixture was stirred at room temperature over night and concentrated in vacuo to afford 126 g of the acid chloride III which was directly used in the next step.

(S)-4-Benzyl-3-(6-benzyloxy-hexanoyl)-oxazolidin-2-one (V)

A solution of 87.7 g (0.50 mol) of (S)-4-benzyl-2-oxazolidininone IV was dissolved in 1.4 l of THF and cooled to −78° C. Hexyllithium (2.5 M in hexanes) (178 ml, 0.45 mol) was added followed by slow addition of a solution of acid chloride III (126 g, 0.50 mol) in 100 ml of THF. After stirring at −78° C. for one additional hour, the resulting solution was allowed to warm to 0° C. Saturated aqueous ammonium chloride solution (400 ml) was added to quench the reaction. The layers were separated and the organic layer was washed with additional 100 ml of saturated ammonium chloride solution. The THF layer was washed twice with 200 ml of 1 M NaOH and with 500 ml of brine, dried over $MgSO_4$ and concentrated. The crude product (162.4 g) was purified by flash chromatography (200 g of SiO$_2$, heptane/TBME=80:20-60:20) to yield 110.1 g (58% over two steps) of the amide V. R$_f$=0.41 (SiO$_2$, 1:1 hexanes-TBME).

(S)-4-Benzyl-3-[(S)-6-benzyloxy-2-methyl-hexanoyl]-oxazolidin-2-one (VI)

A THF (200 ml) solution of the amide V (120.1 g, 0.32 mol) was added to 372 ml (0.37 mol) of NaHMDS (1.0M in THF) in 380 ml of THF at −78° C. followed by the addition of a CH$_3$I (78.4 ml, 1.26 mol) solution in 70 ml of THF. The reaction mixture was stirred for 2 h at −78° C. Aqueous saturated ammonium chloride (670 ml) was added to quench the reaction. The layers were separated and the aqueous phase was extracted with 200 ml of TBME. The combined organic layers were washed twice with 250 ml of brine, dried over MgSO$_4$ and concentrated in vacuo. The product VI (123.9 g) was obtained in 87% de and was directly used in the next step. R$_f$=0.50 (SiO$_2$, 1:1 heptane-TBME);

(S)-6-Benzyloxy-2-methyl-hexan-1-ol (VII)

To a suspension of 13.2 g (0.35 mol) of LiAlH$_4$ in 380 ml of THF was added a solution of amide VI in 250 ml of THF at 0° C. The mixture was stirred for 2 h at 0° C. and quenched with 14 ml of H$_2$O, 14 ml of 15% NaOH and 25 ml of H$_2$O. The precipitated aluminum salts were removed by filtration. After concentration of the filtrate, the crude product was purified by silica gel filtration (570 g of SiO$_2$, toluene/EtOAc=90:10, 3 l and toluene/EtOAc=80:20 1 l). The product VII was obtained as a colorless oil (54.5 g, 81% over two steps). R$_f$=0.24 (SiO$_2$, 1:1 heptane-TBME); HPLC: 87% de (Chiralcel OD, n-hexane/i-PrOH=95:5, 1.0 ml/min, 30° C.) t$_R$=10.07 min.

[(S)-6-Benzyloxy-2-methyl-hexyloxy]-tert-butyl-dimethyl-silane (VIII)

The alcohol VII (54.4 g, 0.25 mol) was dissolved in 100 ml of DMF and treated with 33.3 g (0.49 mol) of imidazole followed by the slow addition of a solution of 55.4 g (0.37 mol) of tert-butyl-dimethylsilylchloride in 100 ml of DMF at 0° C. The mixture was stirred for 2 hours at 20° C., then poured onto 240 ml of ice cold 0.1 N HCl and extracted with 300 ml of heptane. The organic layer was washed with additional 100 ml of 0.1 N HCl, 200 ml of saturated aqueous NaHCO$_3$, 200 ml of brine, dried over MgSO$_4$ and concentrated in vacuo. The crude product (81.5 g) was purified by filtration (670 g of SiO$_2$, toluene) to afford 64.8 g (79%) of a colorless oil. R$_f$=0.64 (SiO$_2$, 1:1 heptane-TBME).

(S)-6-(tert-Butyl-dimethyl-silanyloxy)-5-methyl-hexan-1-ol (IX)

A solution of 64.0 g (0.19 mol) of the benzylether VIII in 500 ml of THF was hydrogenated (3.5 bar) over 7.0 g of 20% Pd(OH)$_2$/C for 30 min at ambient temperature. The catalyst was removed by filtration and the filtrate was concentrated to afford alcohol IX as colorless oil (46.9 g, 100%). R$_f$=0.33 (SiO$_2$, 1:1 heptane-TBME).

tert-Butyl-[(S)-6-iodo-2-methyl-hexyloxy]-dimethyl-silane (X)

Triphenylphosphine (23.91 g, 91.16 mmol) and imidazole (12.45 g, 182.9 mmol) were added to a solution of 15 g (60.9 mmol) of alcohol IX in 390 ml of acetonitrileltoluene (1:5) at room temperature. The mixture was cooled to 0° C. and 23.13 g (91.13 mmol) of iodine was added in 4 portions over a period of 10 min. The heterogenous solution was stirred for 90 min. Aqueous sodium bisulfite (4%, 300 ml) and 100 ml of toluene were added. The aqueous layer was separated and re-extracted with toluene (100 ml). The combined toluene layers were filtered over silica gel and concentrated in vacuo. To the residue was added heptane (225 ml). The resulting suspension was stirred for 10 min. and stored at 4° C. for 12 h. Filtration and concentration of the filtrate afforded 21.05 g (97%) of the iodide X as a pale yellowish oil. R$_f$=0.66 (SiO$_2$, 7:3 heptane-AcOEt).

EXAMPLE 2

Aldehyde 1 with TBDMS Protecting Groups

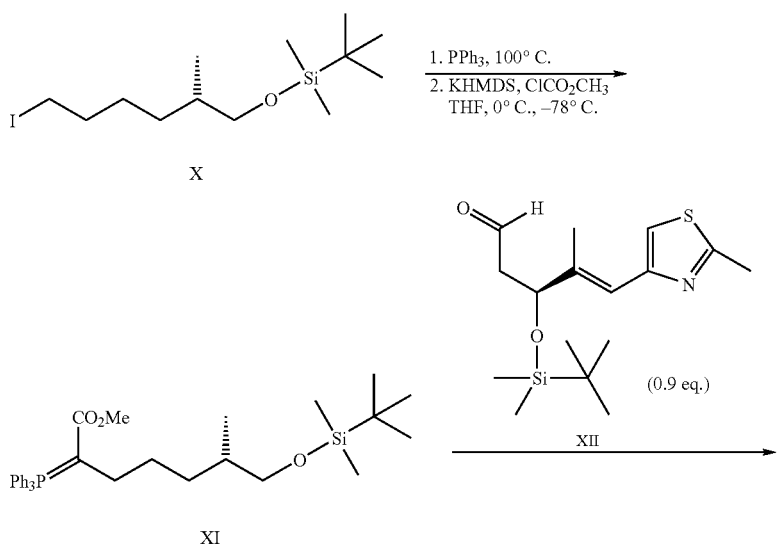

-continued
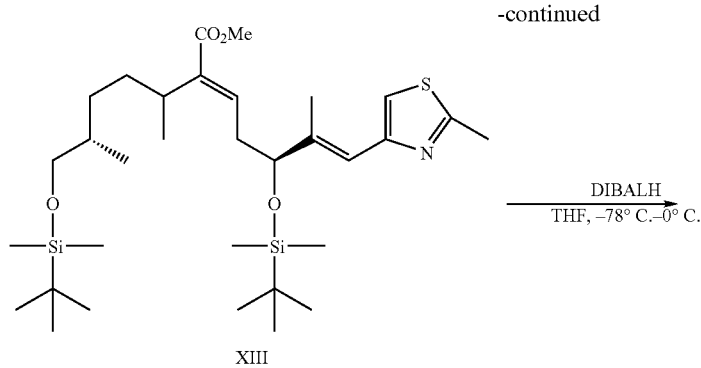
XIII
DIBALH
THF, −78° C.–0° C.
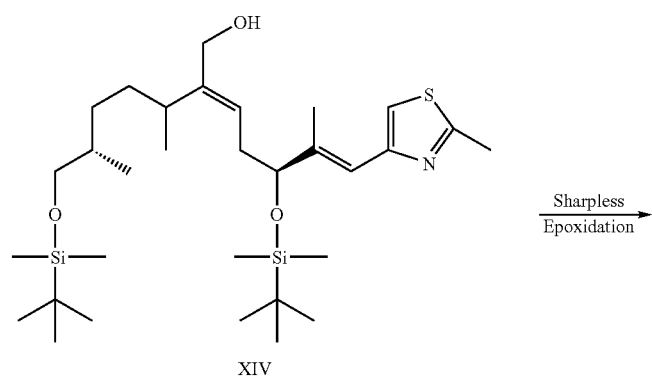
XIV
Sharpless
Epoxidation
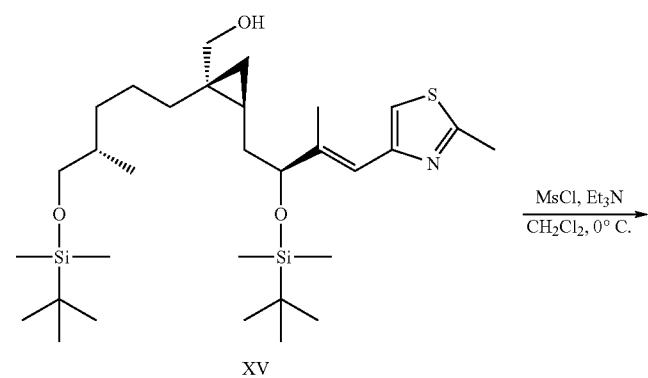
XV
MsCl, Et₃N
CH₂Cl₂, 0° C.
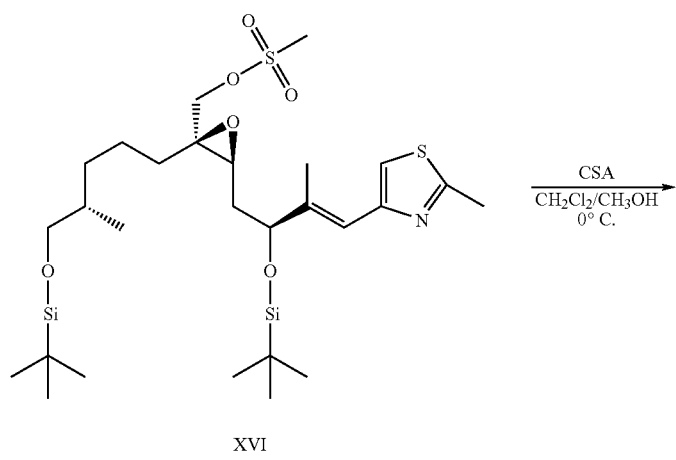
XVI
CSA
CH₂Cl₂/CH₃OH
0° C.

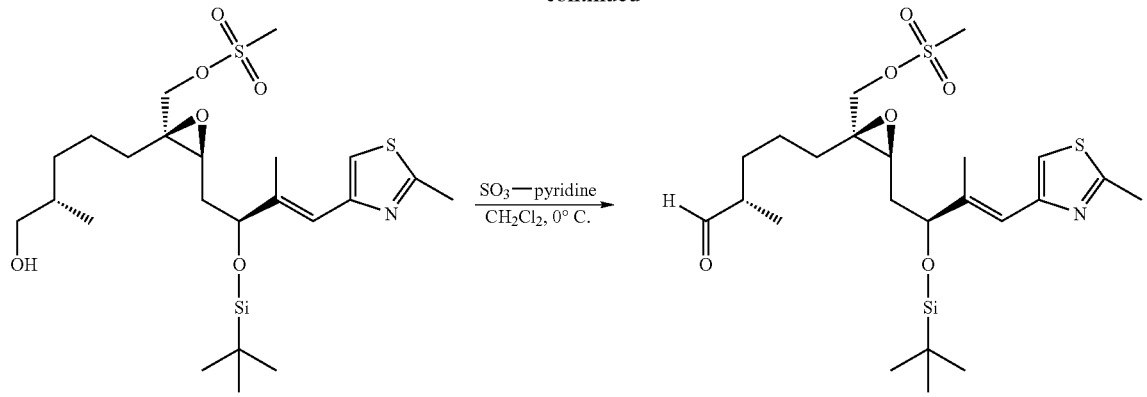

(S)-7-(tert-Butyl-dimethyl-silanyloxy)-6-methyl-2-(triphenylphosphanylidene)-heptanoic acid methyl ester (XI)

Under argon and at room temperature, iodide X (15.46 g, 43.4 mmol) and triphenylphosphine (12.52 g, 45.75 mmol) were added to toluene (8 ml). The resulting mixture was heated at 100° C. for 3 h. Then, toluene was removed under reduced pressure. THF (400 mL) was added to the residue (29.67 g) and the solution was cooled to 0° C. and subsequently treated with a potassium bis(trimethylsilyl)amide solution in toluene (0.5 M, 174 ml, 86.8 mmol). The resulting orange suspension was stirred for 1 h at 0° C. and then cooled down to −75° C. Methyl chloroformate (3.72 ml, 48.2 mmol) was added. After stirring for 1 h at −75° C. the yellowish reaction mixture was allowed to warm-up to −40° C. NaHCO$_3$ (300 ml) was added followed by EtOAc (300 ml) and water (150 ml). The layers were separated and the aqueous phase was extracted with EtOAc (150 ml). The combined organic layers were washed with a saturated aqueous solution of NaCl (2×200 ml), dried over MgSO$_4$ and concentrated in vacuo. The crude product XI (27.02 g) obtained as a viscous orange oil was directly used in the next step.

(2E,6E)-(S)-5-(tert-Butyl-dimethyl-silanyloxy)-2-[(S)-5-(tert-butyl-dimethyl-silanyloxy)-4-methyl-pentyl]-6-methyl-7-(2-methyl-thiazol-4-yl)-hepta-2,6-dienoic acid methyl ester (XIII)

A solution of ylide (XI) (27 g) in toluene (200 ml) at ambient temperature under argon was treated with solution of aldehyde (XII) (12.7 g, 39.0 mmol) in toluene (80 ml). The resulting mixture was stirred at 70° C. for 5 h. The solvent was removed under reduced pressure. The remaining solid residue (37.8 g) was taken in 370 ml of heptane and stirred successively at 40° C. for 30 min, at room temperature for 2 h and 30 min and finally at 0° C. for 30 min. The resulting suspension was filtered and the filtercake was washed with heptane (2×60 ml). The filtrates were collected and concentrated in vacuo to give 24.85 g of the Wittig product XIII as a yellowish oil which was used for the next step without further purification. R$_f$=0.59 (SiO$_2$, 1:1 heptane-AcOEt); $^1$H-NMR (DMSO-d6, 300 MHz, 300 K) □6.90 (s, 1H, C$_{5''}$—H), 6.77 (t, J=7.5 Hz, 1H, C$_3$—H), 6.47 (s, 1H, C$_7$—H), 4.20 (dd, J=7.2, 5.4 Hz, 1H, C$_5$—H), 3.69 (s, 3H, CO$_2$CH$_3$), 3.40 (dd, J=9.9, 5.7 Hz, 1H, C$_{5'}$—H$_a$), 3.31 (dd, J=9.9, 6.6 Hz, 1H, C$_{5'}$—H$_b$), 2.68 (s, 3H, C$_{2''}$—CH$_3$), 2.44-2.36 and 2.28-2.21 (two m, 4H, C$_4$—H$_2$ and C$_{1'}$—H$_2$), 2.00 (s, 3H, C$_6$—CH$_3$), 1.30-1.15 (two m, 4H, C$_{2'}$—H$_2$, C$_{3'}$—H$_a$ and C$_{4'}$—H), 1.06-0.99 (m, 1H, C$_{3'}$—H$_b$), 0.86 (s, 9 H, SiC(CH$_3$)$_3$), 0.85 (s, 9 H, SiC(CH$_3$)$_3$), 0.83 (d, J=6.6, 3H, C$_{5'}$—CH$_3$), 0.05 (s, 3H, SiCH$_3$), 0.01 (s, 6 H, two SiCH$_3$), −0.01 (s, 3 H, SiCH$_3$).

(2E,6E)-(S)-5-(tert-Butyl-dimethyl-silanyloxy)-2-[(S)-5-(tert-butyl-dimethyl-silanyloxy)-4-methyl-pentyl]-6-methyl-7-(2-methyl-thiazol-4-yl)-hepta-2,6-dien-1-ol (XIV)

To 13.9 g (23 mmol) of allylic ester XIII in 500 ml of THF at −78° C. was added over 10 min 47 ml (70 mmol) of DIBALH (1.5 M in toluene). The reaction mixture was successively stirred at −78° C. for 3 h, allowed to warm to 0° C. within 30 min. and further stirred at 0° C. for 30 min. before being quenched by the addition of 50 ml of aqueous 0.1N HCl. The layers were separated and the aqueous layer was washed with TBME (2×50 ml). The combined organic extracts were washed with aqueous saturated NaHCO$_3$ (2×50 ml) and brine (50 ml), dried over MgSO$_4$ and concentrated in vacuo. The crude product was purified by flash-chromatography (SiO$_2$, 5:1 heptane/EtOAc) to afford 10.0 g (76%) of allylic alcohol XIV as a pale yellowish oil. R$_f$=0.16 (SiO$_2$, 3:1 heptane-AcOEt).

{(2S,3S)-3-[((E)-(S)-2-(tert-Butyl-dimethyl-silanyloxy)-3-methyl-4-(2-methyl-thiazol-4-yl)-but-3-enyl]-2-[(S)-5-(tert-butyl-dimethyl-silanyloxy)-4-methyl-pentyl]-oxiranyl}-methanol (XV)

The allylic alcohol (XIV) (3.00 g, 5.28 mmol) was dissolved in 51 ml of CH$_2$Cl$_2$. A 0.59 M solution of (+)-diethyl-L-tartrate (4.48 ml, 2.64 mmol) in CH$_2$Cl$_2$ was added at −30° C. followed by a 0.34 M solution of titanium(IV) isopropoxide (6.21 ml, 2.11 mmol) in CH$_2$Cl$_2$. The mixture was stirred for 30 min at −30° C. Then 2.11 ml (16.6 mmol) of tert-butyl-hydroperoxide (5.5 M in decane) was added over 5 min. The reaction mixture was stirred at −30° C. for 24 h. Aqueous NaHSO$_3$ (4%, 50 ml) was then added. The layers were separated and the aqueous layer was extracted with ethyl acetate (2×50 ml). The combined organic extracts were washed with 50 ml of brine and dried over MgSO$_4$. After concentration in vacuo, 3.11 g of crude epoxy alcohol XV was obtained as a pale yellowish oil which was used for the next step without further purification $R_f$=0.22 (SiO$_2$, 2:1 heptane-AcOEt); MS (ES+) m/z (%) 606 (100, [M+Na]$^+$), 584 (13, [M+H]$^+$).

Methanesulfonic acid (2S,3S)-3-[(E)-(S)-2-(tert-butyl-dimethyl-silanyloxy)-3-methyl-4-(2-methyl-thiazol-4-yl)-but-3-enyl]-2-[(S)-5-(tert-butyl-dimethyl-silanyloxy)-4-methyl-pentyl]-oxiranylmethyl ester (XVI)

To a solution of crude epoxyalcohol (XV) (3.11 g, 5.3 mmol) in CH$_2$Cl$_2$ (40 mL) at 0° C., were added 2.74 mL (16.0 mmol) of N-ethyldiisopropylamine. The resulting mixture was stirred 15 min. at 0° C. Thereupon, methanesulfonyl chloride was added dropwise (0.75 ml, 8.0 mmol). After stirring for 1 h at 0° C., the reaction solution was quenched with 40 mL of H$_2$O and 40 mL of TBME. The layers were separated and the aqueous layer was extracted with TBME (40 ml). The organic extracts were washed with HCl (0.1N) (40 ml), saturated aqueous NaHCO$_3$ (2×40 ml) and brine (40 ml) and dried over MgSO$_4$. Concentration in vacuo provided 3.79 g of crude mesylate XVI which was used for the next step without further purification. Purification. $R_f$=0.27 (SiO$_2$, 2:1 heptane-AcOEt); HRMS m/z 684.3222 ([M+Na]$^+$, C$_{31}$H$_{59}$NO$_6$S$_2$Si$_2$ requires 684.3220).

Methanesulfonic acid (2S,3S)-3-[(E)(S)-2-(tert-butyl-dimethyl-silanyloxy)-3-methyl-4-(2-methyl-thiazol-4-yl)-but-3-enyl]-2-((S)-5-hydroxy-4-methyl-pentyl)-oxiranylmethyl ester (XVII)

The crude TBDMS ether XVI (3.79 g, 5.7 mmol) was dissolved in a mixture of CH$_2$Cl$_2$ and CH$_3$OH (1:1 v/v) (140 ml) and treated at 0° C. with 1.33 g (5.73 mmol) of 10-camphorsulfonic acid. The reaction mixture was stirred for 1 h at 0° C. After completion of the deprotection 20 ml of saturated aqueous NaHCO$_3$ were added along with 20 ml of TBME. The layers were separated and the aqueous layer was extracted with TBME (2×20 mL). The combined organic layers were washed with saturated aqueous NaHCO$_3$ (2×20 ml), brine (20 ml), dried over MgSO$_4$ and concentrated under reduced pressure. The crude product XVII (3.11 g) obtained as a yellowish oil was used for the next step without further purification. $R_f$=0.28 (SiO$_2$, 1:1 heptane-AcOEt).

Methanesulfonic acid (2S,3S)-3-[(E)-(S)-2-(tert-butyl-dimethyl-silanyloxy)-3-methyl-4-(2-methyl-thiazol-4-yl)-but-3-enyl]-2-((S)-4-methyl-5-oxo-pentyl)-oxiranylmethyl ester (1)

A solution of the alcohol XVII (3.11 g, 5.7 mmol) in CH$_2$Cl$_2$ (15 ml) at 0° C. was treated sequentially with triethylamine (10 ml), DMSO (6 ml) and a solution of SO$_3$-pyridine (3.61 g, 22.7 mmol) in DMSO (40 ml) which was added over 5 min. After stirring for 1 h at 0° C., the reaction mixture was quenched with aqueous NaHSO$_4$ (10%, 20 ml) and diluted with TBME (20 ml). The layers were separated and the aqueous layer was extracted with TBME (2×20 mL). The combined organic layers were washed with saturated aqueous NaHCO$_3$ (2×20 ml), brine (20 ml), dried over MgSO$_4$ and concentrated under reduced pressure. The residue was purified by flash chromatography (SiO$_2$, 3:1 heptane/EtOAc). The aldehyde 1 was obtained as a pale yellowish oil (2.20 g, 76% yield over four steps based on XIV). $R_f$=0.39 (SiO$_2$, 1:1 heptane-AcOEt).

EXAMPLE 3

Aldehyde XVI' with TBDMS Protecting Groups

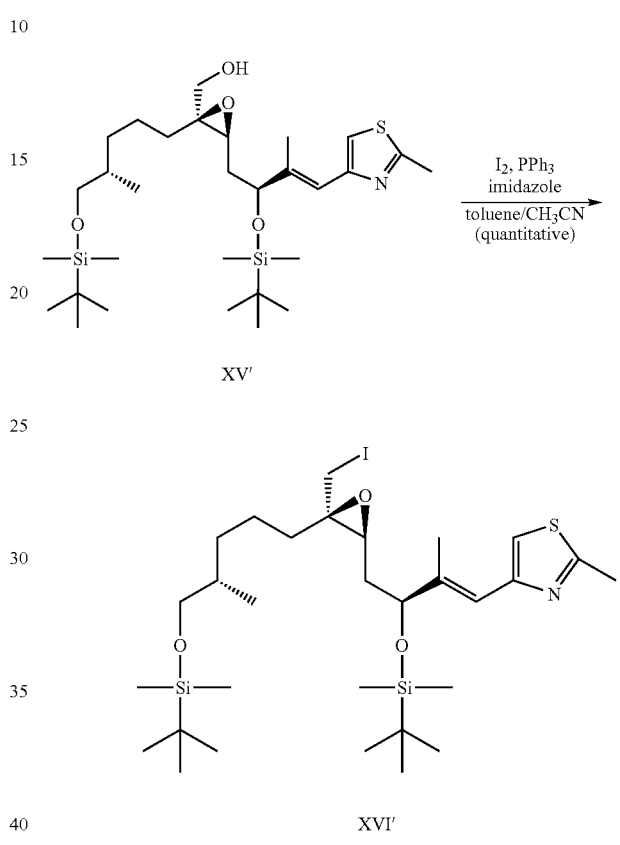

4-[(E)-(S)-3-(tert-Butyl-dimethyl-silanyloxy]-4-{(2S,3R)-3-[(S)-5-(tert-butyl-dimethyl-silanyloxy)-4-methyl-pentyl]-3-iodomethyl-oxiranyl}-2-methyl-but-1-enyl)-2-methyl-thiazole (XVI')

A solution of epoxy-alcohol XV' (50 mg, 86 μmol) triphenylphosphine (34 mg, 0.13 mmol), (50 mg, 86 (34 mg, 0.13 mmol) and imidazole (18 mg, 0.26 mmol) in 5:1 v/v toluene/acetonitrile (2.4 ml) at room temperature under argon was treated with iodine (33 mg, 0.13 mmol) in one portion. After 30 min stirring, the reaction was judged complete (TLC) and was worked-up. The reaction mixture was poured onto aqueous saturated NaHSO$_4$ (5 ml). The layers were separated and the aqueous layer was extracted with toluene (2×2 ml). The combined organic layers were washed with 1N HCl (5 ml), aqueous saturated NaHCO$_3$ (5 ml) and brine (5 ml), dried over MgSO$_4$ and concentrated in vacuo. The residue was suspended in heptane and the insoluble triphenylphosphine oxide was removed by filtration. The crude iodide XVI' was obtained as a pale yellowish oil (65 mg) which did not require further purification.

EXAMPLE 4

Compound 2

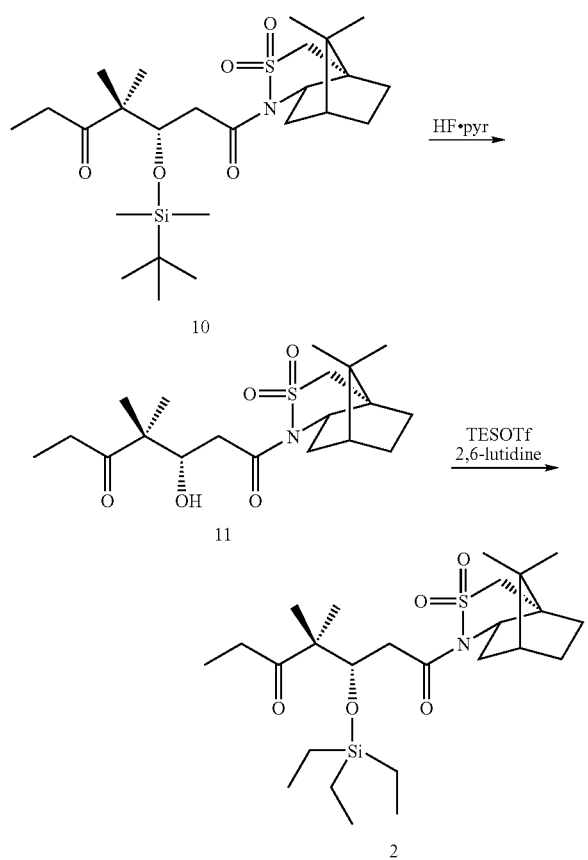

1-(10,10-Dimethyl-3,3-dioxo-6-thia-4-aza-tricyclo
[5.2.1.0]dec-4-yl)-3-hydroxy-4,4-dimethyl-heptane-
1,5-dione (11)

Under argon and in a teflon flask, The TBDMS ether (10) (9.21 g, 18.43 mmol) was mixed with HF.pyridine complex (26.3 ml, 921 mmol) at ambient temperature. The resulting reaction mixture was stirred for 2 h and then quenched by adding it to a stirred aqueous solution of $NaHCO_3$ (78 g in 500 ml of water) along with 200 ml of TBME. The layers were separated and the organic layer was washed with brine (2×200 ml), dried over $MgSO_4$ and concentrated in vacuo to give 6.80 g of crude product which did not require any further purification.

1-(10,10-Dimethyl-3,3-dioxo-6-thia-4-aza-tricyclo
[5.2.1.0]dec-4-yl)-4,4-dimethyl-3-triethylsilanyloxy-
heptane-1,5-dione (2)

To a solution of crude alcohol (11) (6.80 g, 17.6 mmol) in $CH_2Cl_2$ (90 ml) at 0° C., 2,6-lutidine (6.14 ml, 52.9 mmol) was added followed by triethylsilyl trifluoromethane-sulfonate (7.98 ml, 35.3 mmol). The resulting solution was stirred at 0° C. for 30 min. The reaction was carefully quenched by adding 140 ml of 1N HCl along with 150 ml of TBME. The layers were separated and the organic layer was washed successively with 100 ml of saturated aqueous $NaHCO_3$ and 100 ml of brine, dried over $MgSO_4$ and concentrated in vacuo. Purification of the crude product by chromatography ($SiO_2$, 4:6 hexanes/AcOEt), afforded 8.3 g of pure TES-ether 2. (90% over two steps). $R_f$=0.62 ($SiO_2$, 1:1 heptane-AcOEt); $^1$H-NMR (DMSO-d6, 400 MHz, 300 K) δ 4.55 (t, J=5.2 Hz, 1H, $C_3$—H), 3.86 (d, J=14.3 Hz, 1H, $C_{8'}$—$H_b$), 3.83 (t, J=6.1 Hz, 1H, $C_{1'}$—H), 3.66 (d, J=14.2 Hz, 1H, $C_{8'}$—$H_b$), 2.84 (dd, J=17.4, 4.6 Hz, 1H, $C_2$—$H_a$), 2.54 (m, 3H, $C_2$—$H_b$ and $C_7$—$H_2$, partially obscured by DMSO), 2.00-1.92 and 1.87-1.73 (2 m, 6H, $C_{2'}$—$H_2$, $C_{3'}$—H and $C_{5'}$—$H_2$), 1.48-1.20 and 1.34-1.24 (2 m, 2H, $C_{4'}$—$H_2$), 1.10 (s, 3H, $C_4$—$CH_3$), 1.07 (s, 3H, $C_4$—$CH_3$), 0.98 (s, 3H, $C_{9'}$—$CH_3$), 0.95 (s, 3H, $C_{9'}$—$CH_3$), 0.94-0.87 (m, 12H, Si($CH_2CH_3$)$_3$ and $C_7$—$H_3$), 0.60-0.45 (m, 6H, Si($CH_2CH_3$)$_3$); $^{13}$C-NMR (DMSO-d6, 100 MHz, 300 K) δ 215.3, 169.7, 73.1, 65.1, 52.9, 52.7, 49.2, 48.1, 45.1, 40, 38.8, 32.8, 32.1, 26.7, 21.5, 20.9, 21.0, 20.4, 8.5, 7.6, 7.5, 5.4; IR (KBr) $v_{max}$ 2958s, 2913m, 2878s, 1702s, 1391m, 1333s, 1312m, 1267m, 1237m, 1219m, 1166m, 1136s, 1087s, 743m, 539m cm$^{-1}$; MS (ES+) m/z (%) 769 (3, [3M+Ca]$^{2+}$), 538 (6, [M+K]$^+$), 522 (100, [M+Na]$^+$), 519 (17, [2M+Ca]$^{2+}$), 500 (5, [M+H]$^+$).

EXAMPLE 5

Compound 6 with TBDMS Protecting Groups

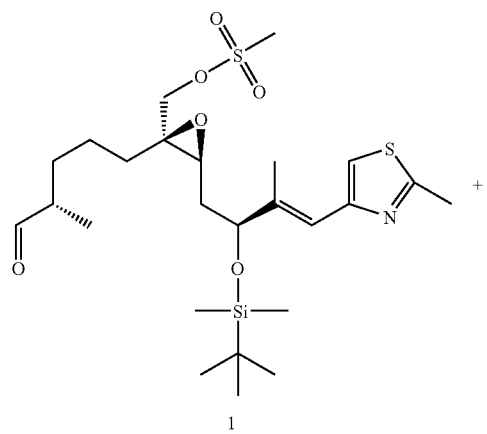

-continued
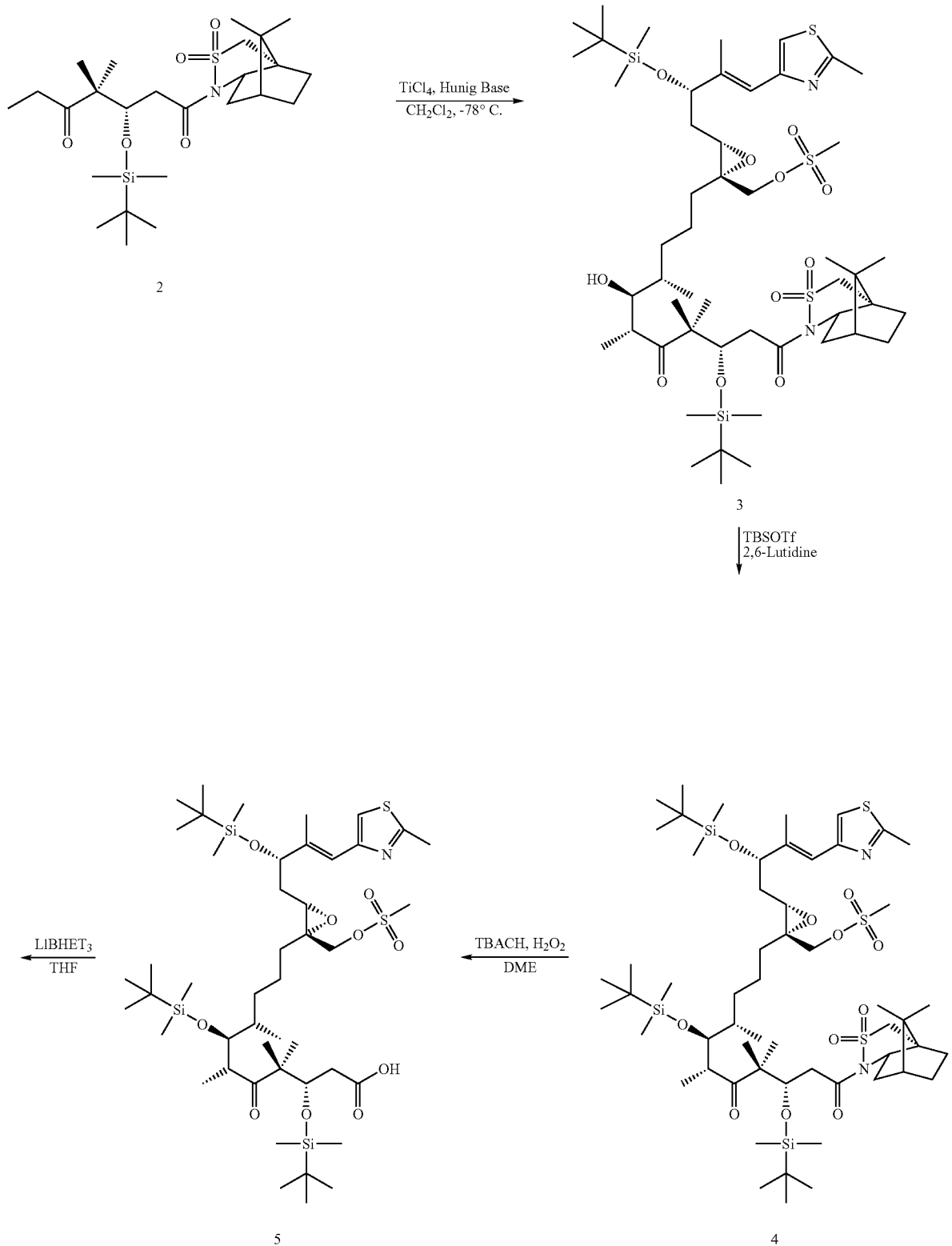

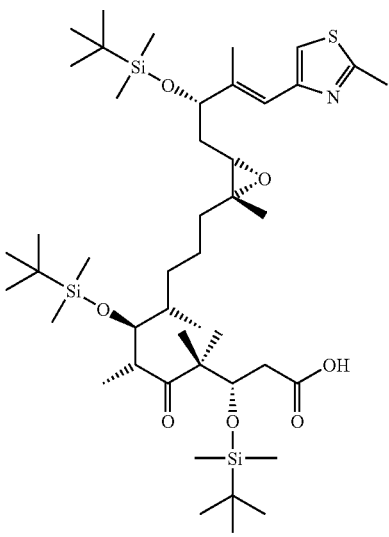

6

Aldol Product (3)

A solution of 2 (750 mg, 1.50 mmol) in CH$_2$Cl$_2$ (5.6 ml) at −78° C. under an atmosphere of argon was treated sequentially with a 0.5 M solution of TiCl$_4$ in CH$_2$Cl$_2$ (3.00 ml, 1.50 mmol) and N-ethyldiisopropylamine (257 □l, 1.50 mmol), whereas the solution developed immediately an intense dark red color. After stirring at −78° C. for 10 min, a solution of 1 (900 mg, 1.65 mmol) in CH$_2$Cl$_2$ (1.9 ml) was added dropwise. Thereupon, the reaction solution was stirred at −78° C. for 1 h then warmed-up at 0° C. and stirred for an additional 15 min at which time the reaction was judged complete (TLC). The reaction was quenched at 0° C. by addition of phosphate buffer (pH 7, 4 ml) and dilution with TBME (5 ml). The aqueous layer was extracted with TBME (2×5 mL). The combined organic extracts were washed with aqueous saturated NaHCO$_3$ (2×4 mL) and brine (4 ml), dried with MgSO$_4$ and concentrated in vacuo. The residue was purified by flash-chromatography (50 g of SiO$_2$, heptane/AcOEt 2:1) to provide the aldol product 3 (1200 mg, 70% based on 1) as a pale yellowish oil. R$_f$=0.42 (SiO$_2$, 1:2 heptane-AcOEt); MS (ES+) m/z (%) 1084 (5, [M+K]$^+$), 1067 (100, [M+Na]$^+$), 1045 (26, [M+H]$^+$).

TBDMS Ether (4)

A solution of 3 (1.20 g, 1.15 mmol) in CH$_2$Cl$_2$ (15 ml) at 0° C. under an atmosphere of argon was treated sequentially with 2,6-lutidine (0.87 ml, 7.49 mmol) and tert-butyldimethylsilyl trifluoromethanesulfonate (1.32 ml, 5.74 mmol). After stirring at 0° C. for 14 h, the reaction was worked-up by addition of 0.1 N aqueous HCl (5 mL) along with CH$_2$Cl$_2$ (5 mL). The layers were separated and the aqueous layer was extracted with CH$_2$Cl$_2$ (2×5 mL). The combined organic extracts were washed successively with aqueous saturated NaHCO$_3$ (2×5 mL) and brine (5 mL), dried with MgSO$_4$ and concentrated in vacuo. The residue was purified by flash-chromatography (50 g of SiO$_2$, heptane/AcOEt 2:1) to provide the compound 16 (893 mg, 67%) as a pale yellowish oil. R$_f$=0.70 (SiO$_2$, 1:2 heptane-AcOEt); MS (ES+) m/z (%) 1197 (12, [M+K]$^+$), 1081 (100, [M+Na]$^+$), 1059 (31, [M+H]$^+$), 599 (75, [M+Ca]$^{2+}$).

Carboxylic Acid (5)

A solution of 4 (318 mg, 0.274 mmol) in 1,2-dimethoxyethane (4.8 ml) at 0° C. was treated sequentially with TBAOH (730 □l, 2.76 mmol) and H$_2$O$_2$ 30% (280 □l, 2.74 mmol) and the resultant mixture was stirred at 0° C. for 5 h before being worked-up: An aqueous saturated solution of NH$_4$Cl (2 ml) was added along with TBME (2 ml). The layers were separated and the aqueous layer was extracted with TBME (2×2 mL). The organic extracts were washed successively with aqueous saturated NaHCO$_3$ (2×2 mL) and brine (2 mL), combined, dried with MgSO$_4$ and concentrated in vacuo. The residue was purified by flash-chromatography (15 g of SiO$_2$, heptane/AcOEt 1:1 containing 1% of AcOH) to provide the compound 5 (103 mg, 39%) as a pale yellowish oil. R$_f$=0.41 (SiO$_2$, 3:3:4 CH$_2$Cl$_2$—CH$_3$CN-hexanes); MS (ES+) m/z (%) 984 (100, [M+Na]$^+$), 962 (12, [M+H]$^+$).

Methyl Epoxide (6)

A solution of 5 (78 mg, 0.081 mmol) in THF (1.6 ml) at ambient temperature was treated dropwise with a 1 M solution of LiBHEt$_3$ in THF (970 □l, 0.97 mmol) and the resultant mixture was stirred at ambient temperature for 1 h. The reaction was quenched by addition of aqueous saturated NH$_4$Cl (2 ml) along with TBME (2 ml). The layers were separated and the aqueous layer was extracted with TBME (2×2 mL). The combined organic extracts were washed successively with aqueous saturated NaHCO$_3$ (2×2 mL) and brine (2 mL), dried with MgSO$_4$ and concentrated in vacuo. The residue was purified by flash-chromatography (6 g of SiO$_2$, heptane/AcOEt 1:1 containing 1% of AcOH) to provide the compound 6 (60 mg, 85%) as a pale yellowish oil. R$_f$=0.56 (SiO$_2$ 1:1 heptane-AcOEt with 1% of AcOH); MS (ES+) m/z (%) 890 (100, [M+Na]$^+$), 868 (50, [M+H]$^+$).

EXAMPLE 6
Aldehyde 1 with One TES and One TBDMS Protecting Group

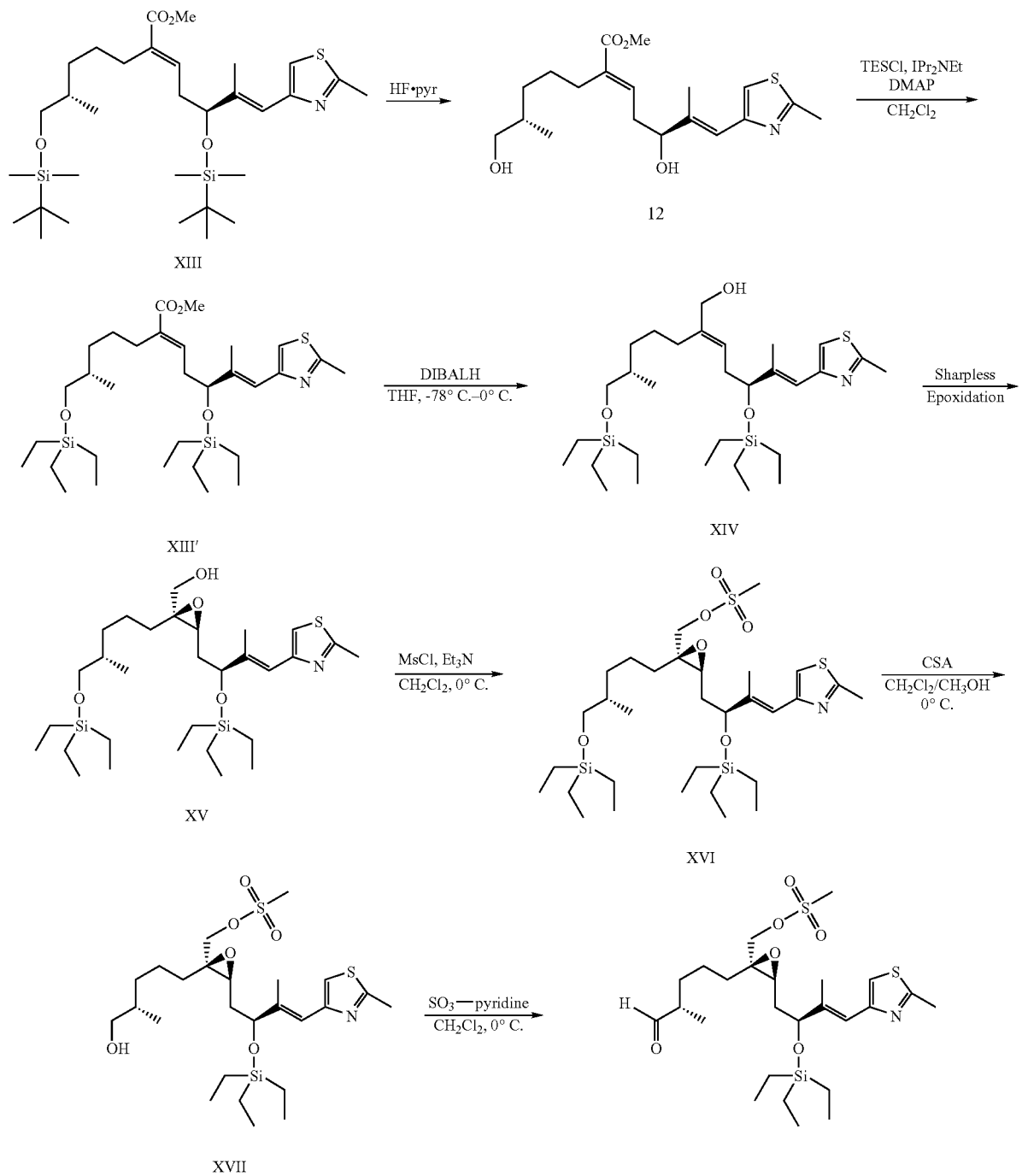

(2E,6E)-(S)-5-Hydroxy-2-[(S)-5'-hydroxy-4'-methyl-pentyl)-6-methyl-7-(2"-methyl-thiazol-4"-yl]-hepta-2,6-dienoic acid methyl ester (12)

In a teflon flask containing 24 ml of HF-pyridine complex (839 mol) at −10° C. the allyl ester (XIII) (10.0 g, 16.8 mmol) was added. The resulting mixture was stirred for 10 min at −10° C. at which time the reaction was judged complete by disappearance of the starting material (TLC) and immediately quenched. The mixture was poured onto a stirred suspension of $NaHCO_3$ (70 g) in water (100 ml) along with TBME (100 ml). The layers were separated and the aqueous phase was extracted with TBME (3×80 ml). The organic extracts were combined and were washed with 150 ml of 0.1N HCl and dried over $MgSO_4$. Concentration in vacuo provided the crude diol (2) (6.34 g) which was directly subjected to the next reaction. $R_f$=0.06 (SiO$_2$, 1:1 heptane-AcOEt); $^1$H-NMR (DMSO-d6, 300 MHz, 300 K) δ 6.90 (s, 1H, C$_{5'''}$—H), 6.75 (t, 1H, J=7.5 Hz, C$_3$—H), 6.51 (s, 1H, C$_7$—H), 4.23 (t, J=6.3 Hz, 1H, C$_3$—H), 3.65 (s, 3H, CO$_2$CH$_3$), 3.41 (dd, J=10.5, 6.0 Hz, 1H, C$_{5'}$—H$_a$), 3.34 (dd, J=10.5, 6.3 Hz, 1H, C$_{5'''}$—H$_b$), 2.64 (s, 3H, C$_{2''}$—CH$_3$), 2.46 (t, J=6.9 Hz, 2H, C$_4$—H$_2$), 2.25 (t, J=7.2 Hz, 2H, C$_{1'}$—H$_2$), 2.00 (s, 3H, C$_6$—CH$_3$), 1.70-1.55 and 1.53-1.25 (2 br m, 6 H, C$_{2'}$—H$_2$, C$_{3'}$—H$_a$, C$_{4'}$—H, C$_5$—OH and C$_{5'}$—OH), 1.15-1.00 (m, 1H, C$_{3'}$—H$_b$), 0.85 (d, J=6.6 Hz, 3H, C$_{4'}$—CH$_3$).

(2E,6E)-(S)-6-Methyl-7-(2'-methyl-thiazol-4'-yl)-2-[(S)-4''-methyl-5''-triethylsilanyloxy-pentyl]-5-triethylsilanyloxy-hepta-2,6-dienoic acid methyl ester (XIII')

A solution of crude diol (12) (6.33 g, 14 mmol) in CH$_2$Cl$_2$ (150 ml) at 0° C., was treated sequentially with N-ethyldiisopropylamine (23.6 ml, 138 mmol), 4-(N,N-dimethylamino)-pyridine (70 mg, 0.57 mmol) and triethylchlorosilane (10.9 ml, 86.1 mmol). The resulting solution was stirred at ambient temperature overnight. The reaction was quenched with a saturated aqueous solution of NaHCO$_3$ (150 ml) and the aqueous layer was extracted with CH$_2$Cl$_2$ (3×200 ml). The organic extracts were combined, washed with 200 ml of brine, dried over MgSO$_4$ and concentrated in vacuo. Purification of the residue by chromatography (SiO$_2$, 20-30% hexanes/AcOEt gradient elution) afforded 8.6 g (86% over two steps) of TES protected diol (XIII'). $R_f$=0.63 (SiO$_2$, 1:1 heptane-AcOEt); $^1$H-NMR (DMSO-d6, 400 MHz, 300 K) δ 7.26 (s, 6, C$_{5'}$—H), 6.73 (t, J=7.3 Hz, 1H, C$_3$—H), 6.48 (s, 1H, C$_7$—H), 4.30 (t, J=6.7 Hz, 1H, C$_5$—H), 3.65 (s, 3H, CO$_2$CH$_3$), 3.41 (dd, J=9.8, 5.9 Hz, 1H, C$_{5''}$—H$_a$), 3.36 (dd, J=9.8, 6.3 Hz, 1H, C$_{5''}$—H$_b$), 2.66 (s, 3H, C$_{2'}$—CH$_3$), 2.45 (t, J=6.7 Hz, 2H, C$_4$—H$_2$), 2.30-2.20 (br m, 2H, C$_{1''}$—H$_2$), 2.04 (s, 3H, C$_6$—CH$_3$), 1.59-1.47 (br m, 1H, C$_{4''}$—H), 1.45-1.23 (br m, 3H, C$_{2''}$—H$_2$ and C$_{3''}$—H$_a$), 1.01-1.00 (br m, 1H, C$_{3''}$—H$_b$), 0.98-0.88 (m, 18H, two Si(CH$_2$CH$_3$)$_3$), 0.83 (d, J=6.9 Hz, 3H, C$_{4''}$—CH$_3$), 0.62-0.52 (m, 12H, two Si(CH$_2$CH$_3$)$_3$); IR (film) ν$_{max}$ 2953s, 2934s, 2913s, 2875s, 1713s, 1644w, 1505w, 1459m, 1437m, 1414w, 1376w, 1285m, 1269m, 1241m, 1185m, 1120m, 1072m, 1006m, 744m, 723s cm$^{-1}$; MS (ES+) m/z (%) 618 (100, [M+Na]$^+$), 596 (72, [M+H]$^+$).

(2E,6E)-(S)-6-Methyl-7-(2'-methyl-thiazol-4'-yl)-2-[(S)-4''-methyl-5''-triethylsilanyloxy-pentyl]-5-triethylsilanyloxy-hepta-2,6-dien-1-ol (XIV)

To a solution of allyl ester (XIII') (45.54 g, 76.4 mmol) in THF (250 ml), was added DIBAL-H 1.5 M in toluene (153 ml, 229 mmol) at −78° C. The resulting mixture was stirred for 3 h at −78° C. The reaction was quenched by slow addition of 115 ml of 2N HCl and diluted with 100 ml of TBME. The layers were separated and the aqueous phase was extracted with TBME (2×100 ml). The combined organic layers were washed with 100 ml of NaHCO$_3$, followed by 100 ml of brine and dried over MgSO$_4$. Concentration in vacuo provided 51.53 g of crude allyl alcohol which was chromatographed (SiO$_2$, 20-40% hexanes/AcOEt gradient elution) to give 32.5 g (75%) of pure allyl alcohol (XIV). $R_f$=0.47 (SiO$_2$, 1:1 heptane-AcOEt); $^1$H-NMR (DMSO-d6, 500 MHz, 300 K) δ 7.29 (s, 1H, C$_{5'}$—H), 6.38 (s, 1H, C$_7$—H), 5.29 (t, J=7.1 Hz, 1H, C$_3$—H), 4.60 (t, J=5.4 Hz, 1H, C$_1$—OH), 4.10 (t, J=6.4 Hz, 1H, C$_5$—H), 3.79 (d, J=5.1 Hz, 2H, C$_1$—H$_2$), 3.40 (dd, J=9.8, 5.9 Hz, 1H, C$_{5''}$—H$_a$), 3.33 (dd, J=9.8, 6.5 Hz, 1H, C$_{5''}$—H$_b$), 2.64 (s, 3H, C$_{2'}$—CH$_3$), 2.25 (t, J=6.8 Hz, 2H, C$_4$—H$_2$), 1.99 (s, 3H, C$_6$—CH$_3$), 2.00-1.90 (br m, 2H, C$_{1''}$—H$_2$), 1.58-1.46 (m, 1H, C$_{4''}$—H), 1.43-1.22 (m, 3H, C$_{3''}$—H$_a$ and C$_{2''}$—H$_2$), 1.08-0.97 (m, 1H, C$_{3''}$—H$_b$), 0.95-0.85 (m, 18H, two Si(CH$_2$CH$_3$)$_3$), 0.82 (d, J=6.7 Hz, 3H, C$_{4''}$—CH$_3$), 0.58-0.50 (m, 12H, two Si(CH$_2$CH$_3$)$_3$); $^{13}$C-NMR (DMSO-d6, 125 MHz, 300 K) □164.1, 152.5, 141.1, 140.7, 119.9, 118.4, 116.6, 78.0, 67.3, 64.6, 35.2, 34.4, 32.9, 28.0, 25.4, 18.9, 16.6, 13.7, 6.74, 6.72, 4.3, 4.0; IR (film) ν$_{max}$ 3341s (br), 2952s, 2932s, 2874s, 1508m, 1458m, 1414m, 1378w, 1238w, 1190m, 1071s, 1016s, 883w, 829w, 743m, 728m cm$^{-1}$; MS (ES+) m/z (%) 590 (28, [M+Na]$^+$), 568 (100, [M+H]$^+$).

{(2S,3S)-3-[(E)-(S)-3'-Methyl-4'-(2''-methyl-thiazol-4''-yl)-2-triethylsilanyloxy-but-3-enyl]-2-[(S)-4'''-methyl-5'''-triethylsilanyloxy-pentyl]-oxiranyl}-methanol (XV)

In a dried flask and under argon, 5.00 g (8.80 mmol) of allyl alcohol (4) was dissolved in 100 ml of CH$_2$Cl$_2$. Molecular sieve 4 Å (4 g) was added and the temperature of the mixture was set to −30° C. (+)-Diethyl-L-tartrate (7.46 ml, 4.40 mmol) followed by titanium(IV)isopropoxide (10.35 ml, 3.52 mmol) were added. The resulting mixture was stirred 1 h at −30° C. whereas the solution gradually developed a yellow-green color. Then, 3.52 ml of tert-butyl-hydroperoxide (19.36 mmol) were added. The reaction was left overnight at −25° C. and was quenched with 100 ml of NaHSO$_3$ and well stirred. The filtrate was extracted with TBME (2×80 ml). The combined organic layers were washed with 80 ml of brine, dried over MgSO$_4$ and concentrated in vacuo to provided 7.24 g of crude product. After purification by chromatography (1:1 hexanes/AcOEt), 5.2 g (100%) of epoxyalcohol (XV) were obtained. $R_f$=0.38 (SiO$_2$, 1:1 heptane-AcOEt); $^1$H-NMR (DMSO-d6, 400 MHz, 300 K) δ 7.28 (s, 1H, C$_{5''}$—H), 6.44 (s, 1H, C$_4$—H), 4.30 (dd, J=8.2, 4.1 Hz, 1H, C$_{2'}$—H), 3.46 (d, J=12.2 Hz, 1H, C$_1$—H$_a$), 3.39 (dd, J=10.2, 6.0 Hz, 1H, C$_{5'''}$—H$_a$), 3.34 (dd, J=10.2, 6.2 Hz, 1H, C$_{5'''}$—H$_b$), 3.27 (d, J=12.2 Hz, 1H, C$_1$—H$_b$), 2.90 (dd, J=7.3, 4.6 Hz, 1H, C$_3$—H), 2.63 (s, 3H, C$_{2''}$—CH$_3$), 1.98 (s, 3H, C$_{3'}$—CH$_3$), 1.81 (ddd, J=12.3, 8.2, 4.6 Hz, 1H, C$_{1'}$—H$_a$), 1.68-1.20 (4 m, 7H, C$_{1'}$—H$_b$, C$_{1'''}$—H$_2$, C$_{2'''}$—H$_2$, C$_{3'''}$—H$_a$, C$_{4'''}$—H,), 1.08-0.98 (m, 1H, C$_{3'''}$—H$_b$), 0.93-0.83 (m, 18H, two Si(CH$_2$CH$_3$)$_3$), 0.82 (d, J=6.7 Hz, 3H, C$_{4'''}$—CH$_3$), 0.59-0.50 (m, 12H, two Si(CH$_2$CH$_3$)$_3$); $^{13}$C-NMR (DMSO-d6, 125 MHz, 300 K) δ 164.7, 152.6, 141.2, 118.7, 117.1, 76.3, 67.6, 63.6, 63.6, 60.2, 57.5, 35.5, 35.4, 33.3, 28.7, 22.3, 19.1, 16.8, 14.4, 13.9, 7.1, 7.0, 4.6, 4.3; IR (film) ν$_{max}$ 3403s (br), 2954s, 2876s, 1507m, 1459m, 1414m, 1377m, 1239m, 1185m, 1084s, 1007s, 976w, 802w, 744s, 676w cm$^{-1}$; MS (ES) m/z (%) 606 (52, [M+Na]$^+$), 584 (100, [M+H]$^+$).

Methanesulfonic acid (2S,3S)-3-[(E)-(S)-3'-methyl-4'-(2''-methyl-thiazol-4''-yl)-2-triethylsilanyloxy-but-3-enyl]-2-[(S)-4'''-methyl-5'''-triethylsilanyloxy-pentyl]-oxiranylmethyl ester (XVI)

To a solution of epoxyalcohol (XV) (11.71 g, 20.0 mmol) in CH$_2$Cl$_2$ (148 ml), was added 10.3 ml (60.1 mmol) of N-ethyldiisopropylamine at 0° C. The resulting mixture was stirred 15 min. at 0° C. Thereupon, methanesulfonylchloride was added (2.33 ml, 30.1 mmol). After stirring for 1 h at 0° C., the reaction solution was quenched with 50 ml of H$_2$O and 50 ml of TBME. The layers were separated and the aqueous layer was washed with TBME (50 ml). The combined organic extracts were washed with 0.1N HCl (40 ml), saturated aqueous NaHCO$_3$ (2×40 ml) and brine (50 ml) and dried over MgSO4. Concentration in vacuo provided 13.7 g of epoxy mesylate (XVI) which did not require any further purification. $R_f$=0.55 (SiO$_2$, 1:1 heptane-AcOEt); $^1$H-NMR (DMSO-d6, 400 MHz, 300 K) δ 7.34 (s, 1H, C$_{5'''}$—H), 6.49 (s, 1H, C$_{4'''}$—H), 4.38 (d, J=11.4 Hz, 1H, C$_1$—H$_a$), 4.34 (dd, J=8.2, 3.7 Hz, 1H, C$_{2''}$—H), 4.07 (d, J=11.4 Hz, 1H, C$_1$—H$_b$), 3.43 (dd, J=9.8, 5.9 Hz, 1H, C$_{5'''-Ha}$), 3.37 (dd, J=9.8, 6.3 Hz, 1H, C$_{5'''}$—H$_b$), 3.33 (s, 3H, SO$_2$CH$_3$), 3.06 (dd, J=7.0, 4.6 Hz, 1H, C$_3$—H), 2.66 (s, 3H, C$_{2'''}$—CH$_3$), 2.03 (s, 3H, C$_{3'}$—CH$_3$), 1.89 (ddd, J=15.2, 7.0, 3.7 Hz, 1H, C$_{1'}$—H$_a$), 1.77-1.20 (5 m, 7H, C$_{1'}$—H$_b$, C$_{1'''}$—H$_2$, C$_{2'''}$—H$_2$, C$_{3'''}$—H$_a$, C$_{4'''}$—H), 1.12-1.03 (m, 1H, C$_{3'''}$—H$_b$), 0.97-0.88 (m, 18H, two Si(CH$_2$CH$_3$)$_3$), 0.85 (d, J=6.6 Hz, 3H, C$_{4'''}$—CH$_3$), 0.63-0.50 (m, 12H, two Si(CH$_2$CH$_3$)$_3$); $^{13}$C NMR (DMSO-d6, 125 MHz, 300 K) δ 164.2, 152.3, 140.5, 118.6, 117.0, 75.8, 72.1, 67.2, 60.4, 57.8, 36.6, 35.1, 34.6, 32.8, 28.1, 21.7, 18.9, 16.5, 13.6, 6.8, 6.7, 4.3, 4.0; MS (ES+) m/z (%) 684 (100, [M+Na]$^+$), 662 (54, [M+H]$^+$).

Methanesulfonic acid (2S,3S)-2-[(S)-5'-hydroxy-4'-methyl-pentyl]-3-[(E)-(S)-3"-methyl-4"-(2"'-methyl-thiazol-4"'-yl)-2-triethylsilanyloxy-butnyl]-oxiranyl-methyl ester (XVII)

A solution of bis-TES ether (XVI) (4.89 g, 7.38 mmol) in THF/AcOH/H$_2$O (10:2:1 v/v/v, 115 ml) was heated at 50° C. for 15 h. To quench the reaction, 460 ml of saturated aqueous solution of NaHCO$_3$ was added and the mixture was extracted with TBME (2×250 ml). The organic layers were combined and washed with brine, dried over MgSO$_4$ and concentrated in vacuo to give 4.73 g of crude product. Purification by flash-chromatography (SiO$_2$; 30-60% AcOEt/hexane gradient elution) afforded 3.10 g (79% over two steps based on XV) of alcohol (XVII). $R_f$=0.15 (SiO$_2$, 1:1 heptane-AcOEt); $^1$H-NMR (DMSO-d6, 400 MHz, 300 K) δ 7.42 (s, 1H, C$_{5'''}$—H), 6.50 (s, 1H, C$_{4'''}$—H), 4.38 (d, J=11.3 Hz, 1H, C$_1$—H$_a$), 4.36 (dd, J=8.3, 4.6 Hz, 1H, C$_{2''}$—H, partially obscured by C$_1$—H$_a$), 4.07 (d, J=11.8 Hz, 1H, C$_1$—H$_a$), 3.30-3.23 (m, 1H, C$_{5'}$—H$_a$), 3.20 (s, 3H, SO$_2$CH$_3$), 3.22-3.14 (m, 1H, C$_{5'}$—H$_b$, partially obscured by SO$_2$CH$_3$), 3.06 (dd, J=7.1, 4.4 Hz, 1H, C$_3$—H), 2.67 (s, 3H, C$_{2'''}$—CH$_3$), 2.04 (s, 3H, C$_{3'}$—CH$_3$), 1.90 (ddd, J=14.2, 8.3, 4.4 Hz, 1H, C$_{1'}$—H$_a$), 1.70-1.58 (m, 1H, C$_{1'}$—H$_b$), 1.54-1.32 (m, 6H, C$_{1'}$—H$_2$, C$_{2'}$—H$_2$, C$_{3'}$—H$_a$, C$_{4'}$—H), 1.10-0.98 (m, 1H, C$_{3'}$—H$_b$), 0.93 (t, J=8.0 Hz, 9H, Si(CH$_2$CH$_3$)$_3$), 0.84 (d, J=6.6 Hz, 3H, C$_{4'}$—CH$_3$), 0.60 (q, J=8.0 Hz, 6H, Si(CH$_2$CH$_3$)$_3$); $^{13}$C-NMR (DMSO-d6, 100 MHz, 300 K) δ 165.1, 153.2, 141.5, 119.4, 117.9, 76.6, 73.3, 67.0, 61.2, 58.6, 37.6, 36.0, 35.5, 33.9, 29.0, 22.6, 19.7, 17.5, 14.9, 14.5, 7.63, 7.58, 5.1; IR (film) σ$_{max}$ 3410s (br), 2955s, 2876s, 1655w, 1505w, 1459m, 1414m, 1359s, 1270w, 1239w, 1177s, 1081m, 1006m, 958m, 833m, 745m, 529m cm$^{-1}$; MS (ES+) m/z (%) 586 (5, [M+K]+), 570 (100, [M+Na]$^+$), 548 (8, [M+H]$^+$).

Methanesulfonic acid (2S,3S)-3-[(E)-(S)-3'-methyl-4'-(2"-methyl-thiazol-4"-yl)-2-triethylsilanyloxy-but-3-enyl]-2-[(S)-4'''-methyl-5'''-oxo-pentyl]-oxiranylm-ethyl ester (1)

To a solution of alcohol (XVII) (2.00 g, 3.65 mmol) in CH$_2$Cl$_2$ (10 ml) at 0° C. was added sequentially triethylamine (3.86 ml, 27.7 mmol), DMSO (6.48 ml, 91.3 mmol) and pyridinium.SO$_3$ complex (2.32 g, 14.6 mmol) in DMSO (26 ml). The resulting solution was stirred 1 h at 0° C. The reaction was quenched with a aqueous solution of NaHSO$_4$ (40%, 120 ml) and TBME (150 ml). The layers were separated and the organic layer was washed with saturated aqueous NaHCO$_3$ (2×100 ml). These aqueous layers were back-extracted with TBME (2×100 ml). The organic extracts were combined and washed with brine (100 ml), dried over MgSO$_4$ and concentrated in vacuo to give 1.94 g of crude product. Purification by flash-chromatography (SiO$_2$, 50-70% AcOEt/hexane gradient elution) provided 1.63 g (82%) of pure aldehyde (1). $R_f$=0.30 (SiO$_2$, 1:1 heptane-AcOEt); $^1$H-NMR (CDCl$_3$, 500 MHz, 300 K) δ 9.61 (d, J=1.7 Hz, 1H, CHO), 6.95 (s, 1H, C$_{5'''}$—H), 6.52 (s, 1H, C$_{4'}$—H), 4.33 (dd, J=4.4 Hz, 1H, C$_2$—H, partially obscured by C$_1$—H$_a$), 4.34 (d, J=11.4 Hz, 1H, C$_1$—H$_a$), 4.08 (d, J=11.4 Hz, 1H, C$_1$—H$_b$), 3.11 (dd, J=7.8, 3.9 Hz, 1H, C$_3$—H), 3.05 (s, 3H, SO$_2$CH$_3$), 2.71 (s, 3H, C$_{2'''}$—CH$_3$), 2.33 (m, 1H, C$_{4'''}$—H), 2.02 (s, 3H, C$_{3'}$—CH$_3$), 1.99-1.32 (6 m, 8H, C$_{1'}$—H$_2$, C$_{1'''}$—H$_2$, C$_{2'''}$—H$_2$, C$_{3'''}$—H$_2$), 1.11 (d, J=7.1 Hz, 3H, C$_{4'''}$—CH$_3$), 0.94 (t, J=8.0 Hz, 9H, Si(CH$_2$CH$_3$)$_3$), 0.61 (q, J=8.0 Hz, 6H, Si(CH$_2$CH$_3$)$_3$); $^{13}$C-NMR (CDCl$_3$, 125 MHz, 300 K) δ 204.7, 164.8, 152.8, 141.8, 119.2, 115.8, 76.0, 72.0, 60.7, 59.0, 46.3, 37.8, 35.3, 30.5, 28.3, 22.5, 19.4, 14.1, 13.5, 7.0, 4.9; IR (film) ν2956s, 2876s, 2720w, 1724s, 1658w, 1508m, 1459m, 1414w, 1358s, 1240w, 1177s, 1079m, 1006m, 957m, 883w, 828m, 745m, 529m cm$^{-1}$; MS (ES+) m/z 546 (100, [M+H]$^+$). MS (ES+) m/z 546 (100, [M+H]$^+$).

What we claim is:

1. A process for the preparation of epothilone derivatives of formula 9:

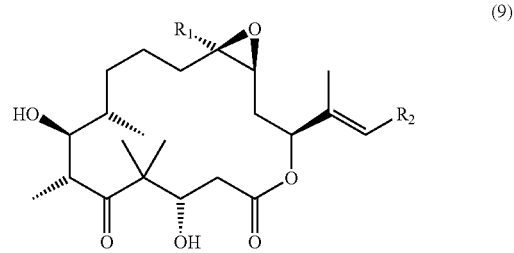

(9)

R1 is methyl;
R2 is an unsubstituted or substituted aryl; an unsubstituted or substituted heteroaryl; or an unsubstituted or substituted heterocyclic radical fused to a benzene nucleus;
comprising the steps of:
a) reacting a compound of formula 1:

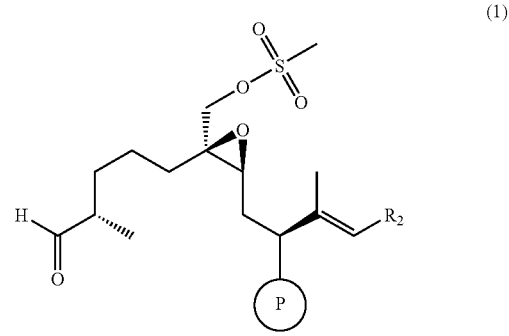

(1)

wherein R2 has the meanings given above; wherein a mesylate group of the compound of formula 1 may be replaced with a tosylate group; and

is an alcohol protecting group;
with a compound of formula 2:

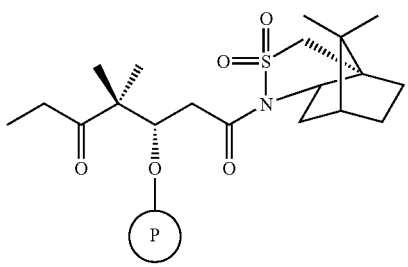

(2)

in the presence of a Lewis acid and addition of a base in an inert solvent to yield a compound of formula 3:

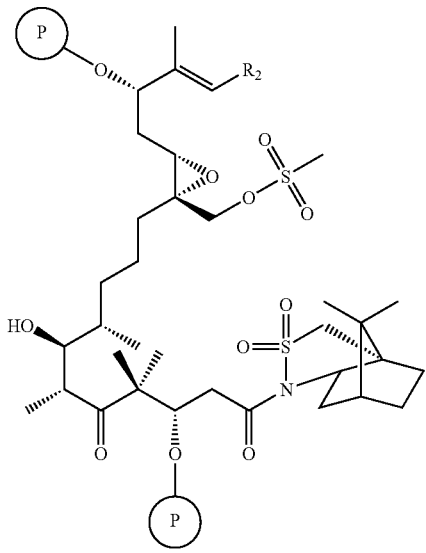

(3)

wherein $R_2$ and

have the above given meanings and wherein a mesylate group of the compound of formula 3 may be replaced with a tosylate group;
b) the reacting compound of formula 3 in the presence of a silyl-ether forming compound to produce the compound of formula 4:

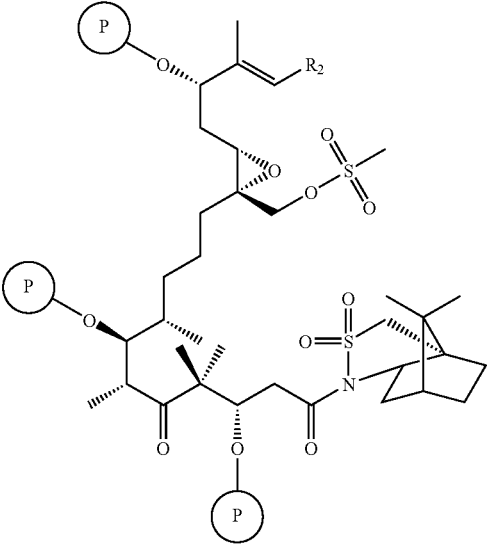

(4)

wherein $R_2$ and

have the meanings given above and wherein a mesylate group of the compound of formula 4 may be replaced with a tosylate group;
c) converting the compound of formula 4 to produce a compound of formula 5:

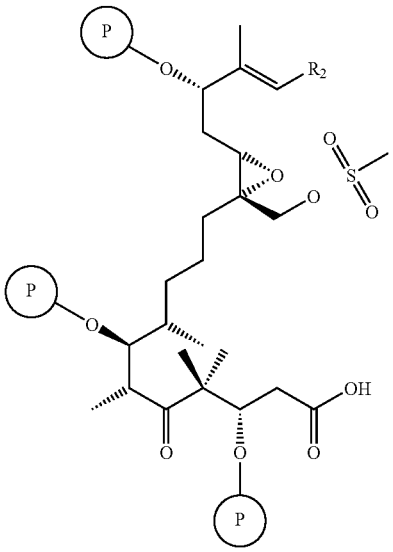

(5)

wherein R2 and

have the meanings given above and wherein the mesylate group of the compound of formula 5 may be replaced with a tosylate group;

d) reacting compounds of above formula 5 with a reducing reagent in an inert solvent to yield a compound of formula 6:

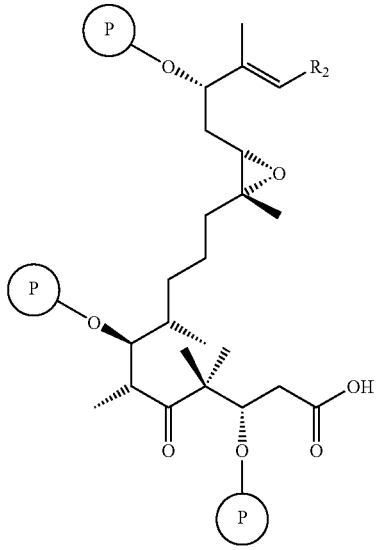

(6)

wherein R2 and the

above have given meanings;

e) hydrolysing the compound of formula 6, to produce a compound of formula 7:

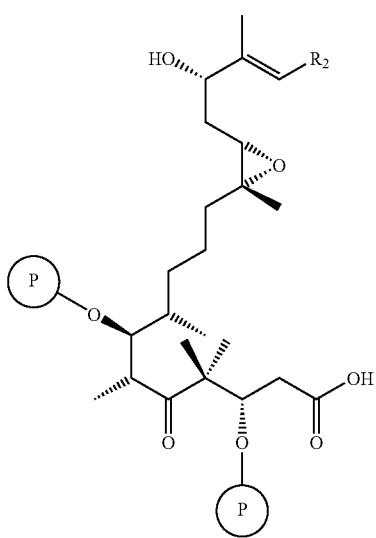

(7)

wherein R2 and

have the above given meanings;

f) macrolactonizing a compound of formula 7, to produce the epothilone derivative of formula 8:

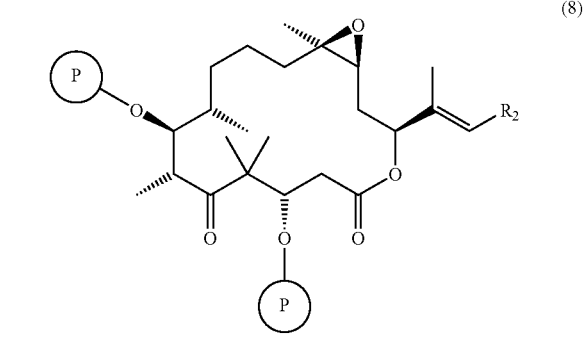

(8)

wherein R2 and

have has the above defined meanings; and g) treating the compound of formula 8 with HF·pyridine in an inert solvent to produce the epothilone derivatives of formula 9.

2. The process according to claim 1, wherein in step a) the compound of formula 1 is reacted with the compound of formula 2 in the presence of TiCl4 and Hünig base (iPr2Net) in dichloromethane.

3. The process according to claim 1, wherein in step b) the compound of formula 3 is reacted with a silyl-ether forming compound in the presence of 2,6-lutidine in dichloromethane.

4. The process according to claim 1, wherein in step c) the compound of formula 4 is converted by splitting off the chiral auxiliary group with TBAOH/H2O2 in DME or LiO2H in THF/MeOH/H2O.

5. The process according to claim 1, wherein in step d) the compound of formula 5 is reacted with LiBHEt3 in THF.

6. The process according to claim 1, wherein in step e) the compound of formula 6 is hydrolysed with TASF or HF pyridine in an inert solvent.

7. The process according to claim 1, wherein in step f) the compound of formula 7 is macrolactonized by treating with Et3N and 2,4,6-trichlorobenzoyl chloride and subsequently reacted with a solution of 4-DMAP in toluene.

8. The process according to claim 1 wherein a mesylate group of the compound of formula 1 is not replaced with a tosylate group.

9. The process according to claim 1 where step a) first occurs at lower temperatures between −50° to −100° C. and thereafter elevated to temperatures between −20° to +20° C. to obtain the compound of formula 3.

10. The process according to claim 1 wherein step b) occurs at temperature between −7° and 25° C.

11. The process according to claim 1 wherein step e) the compound of formula 6 is hydrolyzed with a desilylation reagent or an acid in an inert solvent.

12. The process according to claim 11 wherein the acid in an inert solvent is TASF in THF or HF-pyridine in THF.

13. The process according to claim 1 where step a) occurs at a temperature between 0° C. and 30° C.

* * * * *